US008674326B2

(12) United States Patent
Iwata

(10) Patent No.: US 8,674,326 B2
(45) Date of Patent: *Mar. 18, 2014

(54) DRIVING TYPE PATIENT PLATFORM, CONTROL DEVICE FOR DRIVING TYPE PATIENT PLATFORM, CONTROL PROGRAM FOR DRIVING TYPE PATIENT PLATFORM, AND PARTICLE BEAM THERAPY SYSTEM UTILIZING THESE ITEMS

(75) Inventor: Takaaki Iwata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/494,371

(22) Filed: Jun. 12, 2012

(65) Prior Publication Data
US 2012/0248331 A1 Oct. 4, 2012

Related U.S. Application Data

(62) Division of application No. 13/009,359, filed on Jan. 19, 2011, now Pat. No. 8,242,465.

(30) Foreign Application Priority Data

Mar. 5, 2010 (JP) ................................ 2010-049150

(51) Int. Cl.
*A61B 6/04* (2006.01)

(52) U.S. Cl.
USPC ........... 250/491.1; 250/492.3; 5/601; 378/209

(58) Field of Classification Search
USPC ........... 250/491.1, 492.1, 492.3; 378/65, 208, 378/209; 5/600, 601, 608
See application file for complete search history.

(56) References Cited

U.S. PATENT DOCUMENTS

| 5,661,654 | A | 8/1997 | Nagashima |
| 6,094,760 | A * | 8/2000 | Nonaka et al. .................... 5/601 |

(Continued)

FOREIGN PATENT DOCUMENTS

| CN | 101217913 A | 7/2008 |
| JP | 7-299697 | 11/1995 |

(Continued)

OTHER PUBLICATIONS

Office Action from Chinese Patent Office dated May 6, 2013, issued in corresponding Chinese Patent Application No. 201110051641.6, with English translation thereof. (15 pages).

*Primary Examiner* — Robert Kim
*Assistant Examiner* — David E Smith
(74) *Attorney, Agent, or Firm* — Buchanan Ingersoll & Rooney PC

(57) ABSTRACT

A patient platform for making the position and posture of a diseased site coincide with those established by a treatment plan. Translation units translate a top board in the X, Y and Z directions respectively, in a fixed coordinate system. Rotation units rotate the top board in the $\theta$, $\phi$, and $\xi$ directions respectively. A controller controls the translation units and rotation units, based on desired rotation center point and desired rotation angle. The controller has a rotation drive signal generation unit that generates a signal for moving the top board in a rotating manner from the reference state "a" of the translation units and the rotation units to a desired rotation angle; and a translation drive signal generation unit that generates a signal for translating the translation units so the amount of translation movement, of the desired rotation center point, caused by the rotation movement is a predetermined value.

16 Claims, 24 Drawing Sheets

(56) References Cited

U.S. PATENT DOCUMENTS

| | | | |
|---|---|---|---|
| 7,373,676 B2 * | 5/2008 | Markovic et al. | 5/601 |
| 8,242,465 B2 * | 8/2012 | Iwata | 250/491.1 |
| 2005/0028280 A1 * | 2/2005 | Nakamura et al. | 5/601 |
| 2005/0228255 A1 | 10/2005 | Saracen et al. | |
| 2005/0234327 A1 * | 10/2005 | Saracen et al. | 600/407 |
| 2006/0203958 A1 * | 9/2006 | Nagamine et al. | 378/20 |
| 2007/0230660 A1 | 10/2007 | Herrmann | |
| 2010/0237257 A1 | 9/2010 | Saracen et al. | |
| 2010/0275927 A1 | 11/2010 | Saracen et al. | |
| 2012/0174317 A1 | 7/2012 | Saracen et al. | |
| 2013/0025055 A1 | 1/2013 | Saracen et al. | |

FOREIGN PATENT DOCUMENTS

| | | |
|---|---|---|
| JP | 11-313900 A | 11/1999 |
| JP | 2005-052236 | 3/2005 |
| WO | WO 2005/099578 A2 | 10/2005 |
| WO | WO 2006/034973 A1 | 4/2006 |
| WO | 2006/124434 A | 11/2006 |

* cited by examiner

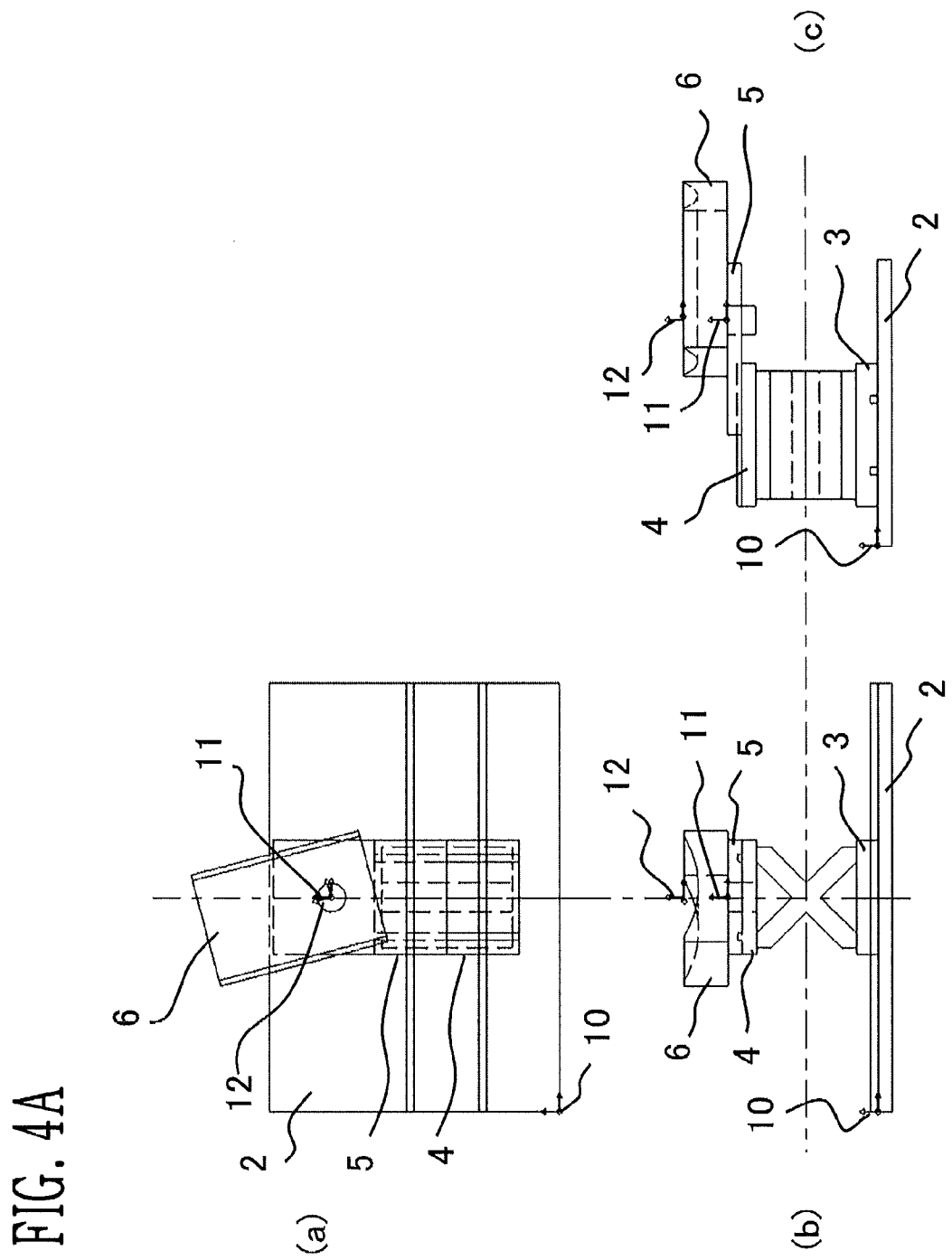

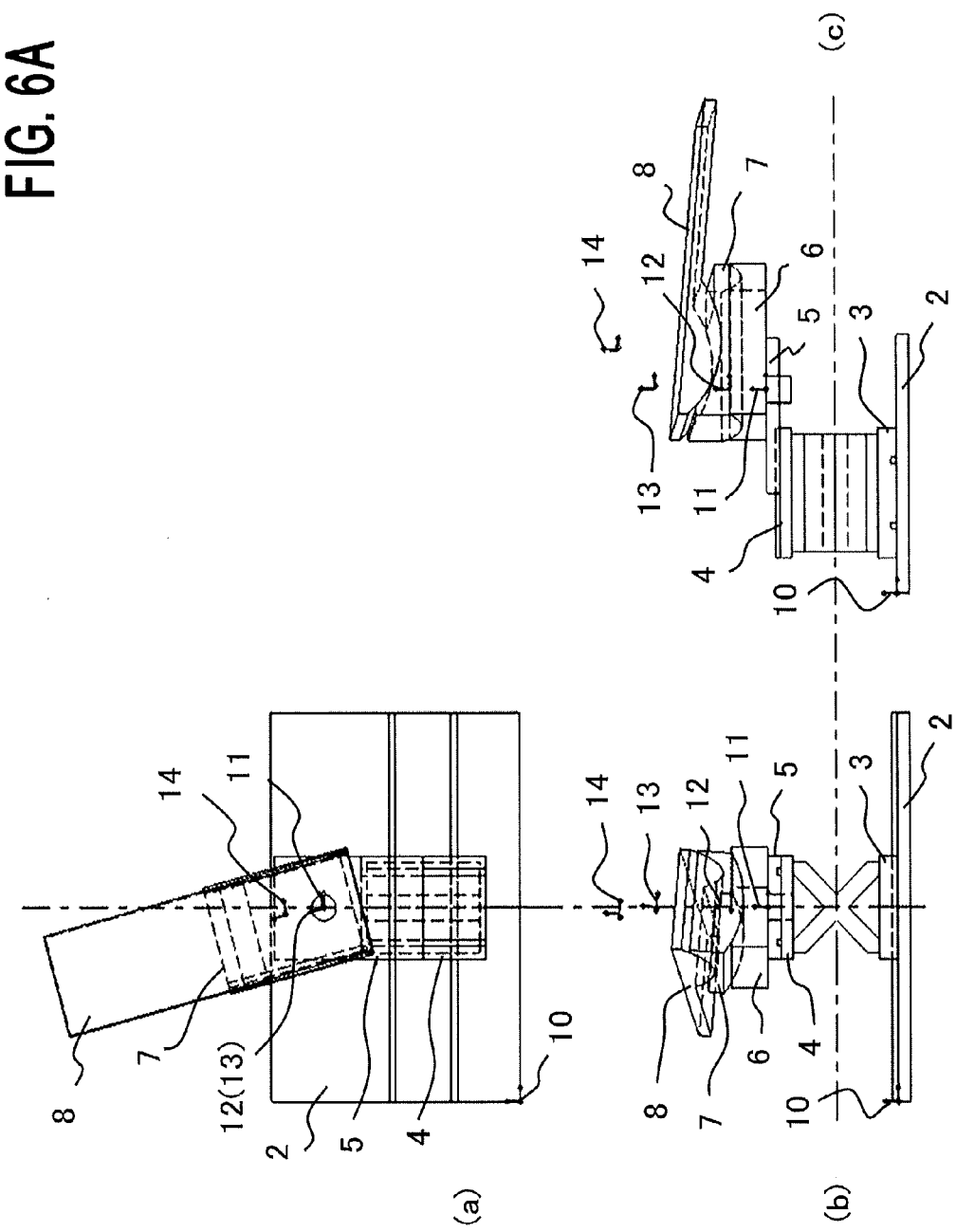

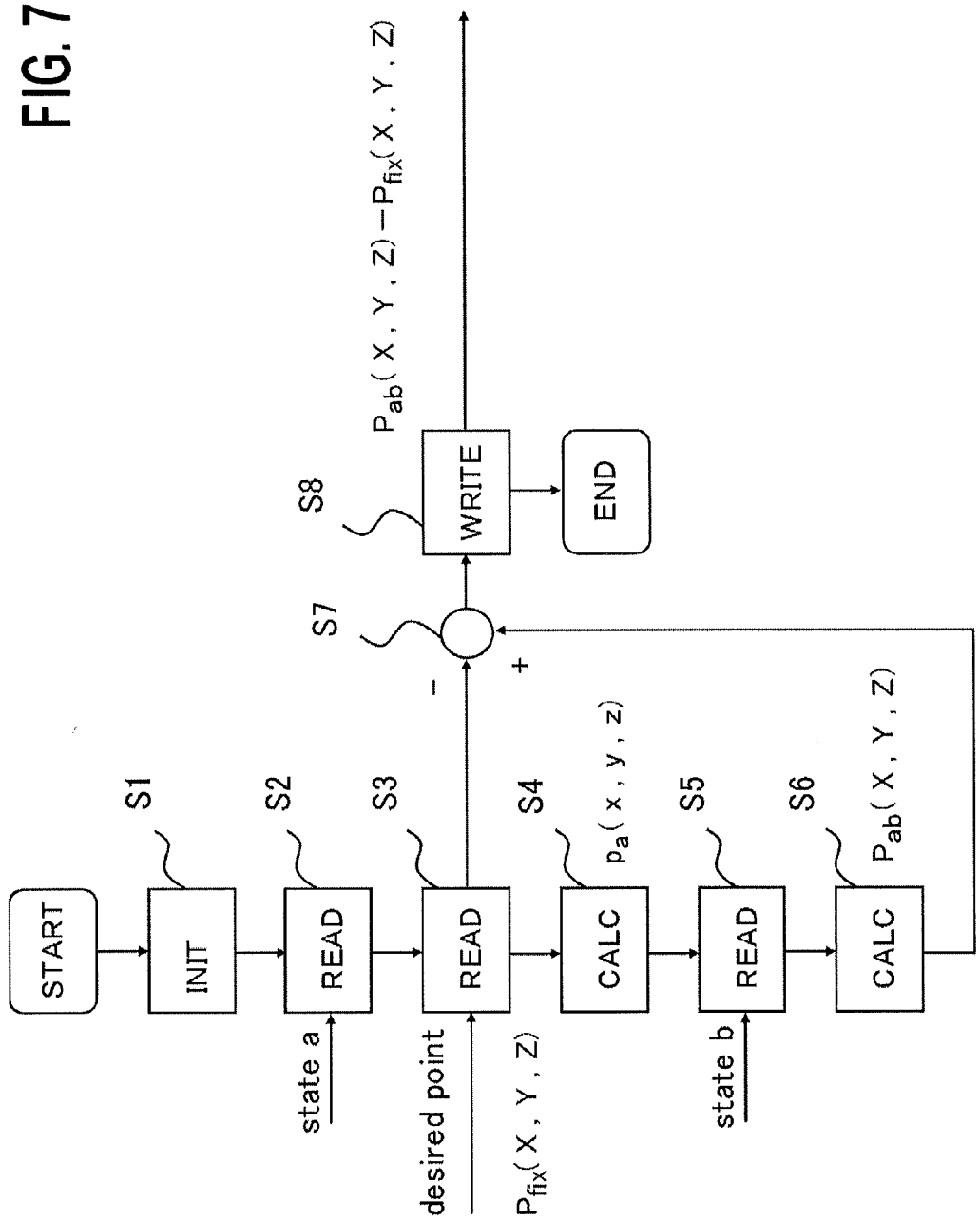

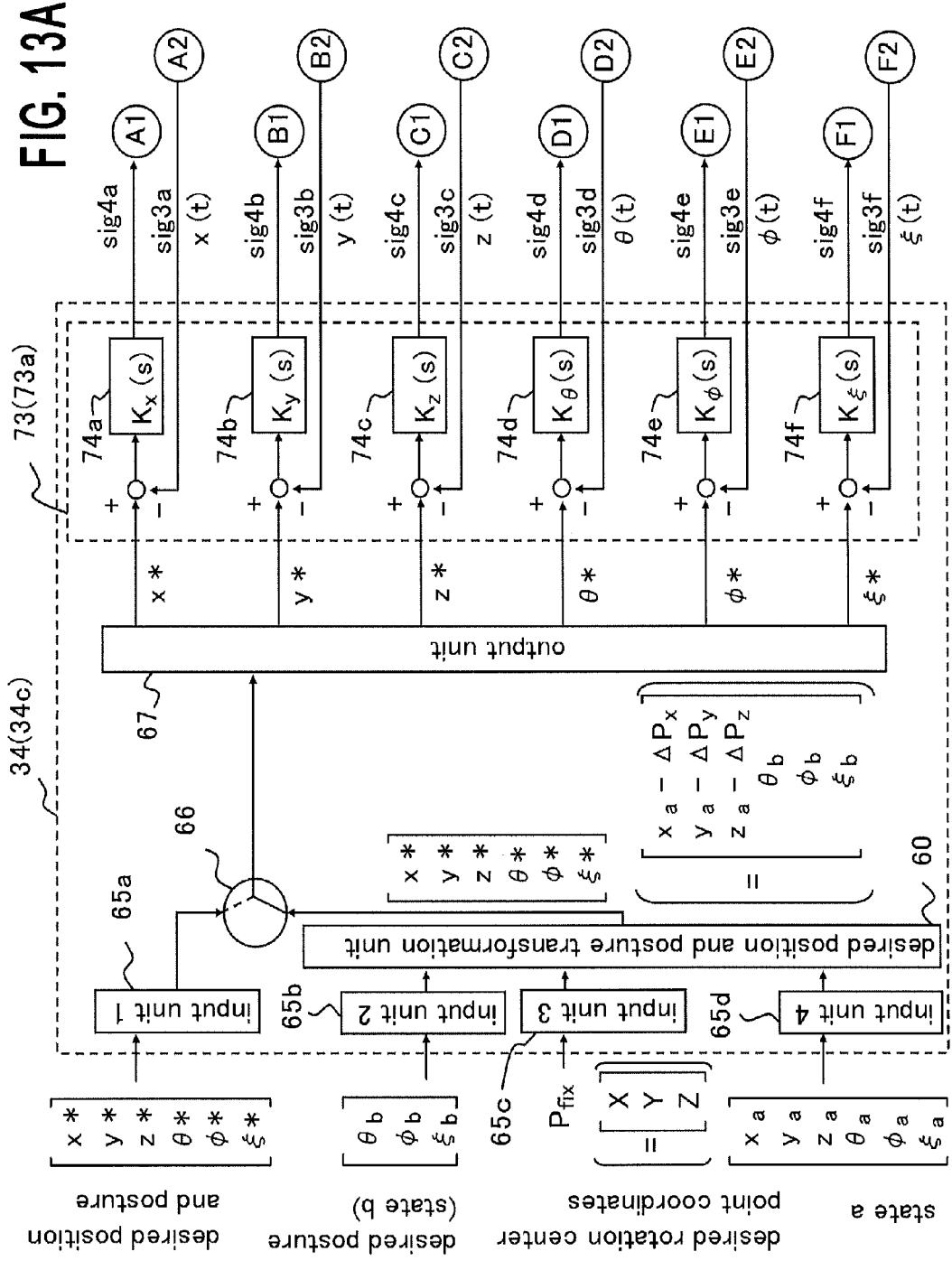

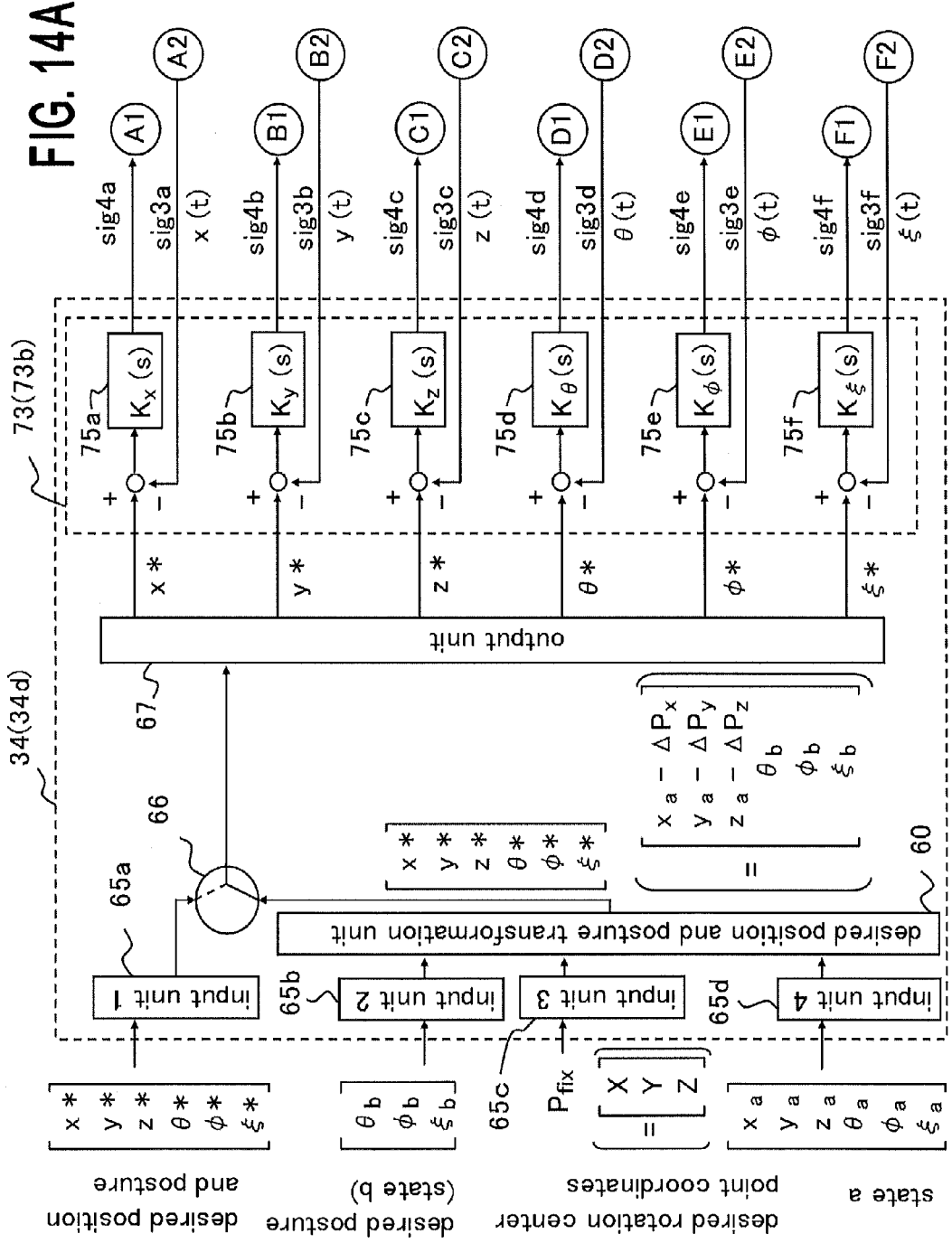

DRIVING TYPE PATIENT PLATFORM, CONTROL DEVICE FOR DRIVING TYPE PATIENT PLATFORM, CONTROL PROGRAM FOR DRIVING TYPE PATIENT PLATFORM, AND PARTICLE BEAM THERAPY SYSTEM UTILIZING THESE ITEMS

BACKGROUND OF THE INVENTION

1. Field of the Invention

The present invention relates to a particle beam therapy system and a radiation therapy system utilized in the medical and R&D fields and particularly to a driving type patient platform, a control device for the driving type patient platform, and a control program for the driving type patient platform.

2. Description of the Related Art

To date, with the development of medical apparatuses and the advancement of medicine, medical apparatuses have been sophisticated and there have been emerging the types of medical apparatuses, which have not been seen before. For example, to date, the treatment through surgery, medication and/or radiation has been dominant in the cancer treatment; however, recently, much attention has been attracted by a particle beam therapy system that performs treatment by irradiating a particle beam exemplified by a proton beam or a carbon beam. The greatest characteristic of the treatment through a particle beam therapy system is that it is low-invasive, whereby the after-therapy QOL (Quality of Life) of a patient can be maintained. At present, particle beam therapy systems are working or under construction at approximately 10 facilities in total in Japan; some of the facilities are reportedly treating as many as 1,000 patients a year.

Accordingly, with regard to a bed, a chair, or the like (hereinafter, referred to as a "patient platform") on which a patient is situated when undergoing a particle beam therapy, a function suitable for particle beam therapy is required; in addition, it leads to the contribution to the growth of the medical apparatus industry to develop a patient platform having a function suitable for particle beam therapy so as to produce a better medical apparatus.

Speaking briefly, a particle beam therapy system irradiates a particle beam in a pinpoint manner in accordance with the shape of a diseased site. For that purpose, it is required that the doctor or engineer (referred to as a "engineer or the like", hereinafter) who operates the particle beam therapy system has to perform the work in which, assuming that the isocenter, which is an irradiation center, is a reference position, the position and the posture of the diseased site is made to coincide with planned values, i.e., the positioning work so that a particle beam can be irradiated in accordance with the shape of the diseased site. In the positioning work, while the position of a diseased site is being monitored by an X-ray image-capturing device, the angle adjustment for a treatment table is implemented in such a way that a particle beam is irradiated onto the diseased site along a direction determined at the stage of making a treatment plan; however, because this positioning work takes a long time, it is required to efficiently perform the positioning work.

In order to realize irradiation onto a patient fixed on the surface of a treatment bed from an arbitrary direction and with an arbitrary distance, especially, non-conplanar irradiation in which the irradiation direction is not perpendicular to the patient center axis, there has been proposed a radiation-therapy bed system (refer to Japanese Patent Application Laid-Open No. 1999-313900). In the radiation-therapy bed system, there are inputted patient position data (in an X-Y-Z coordinate system) and proton beam radiation angle, which are calculated when therapy simulation is performed; these data items (position and angle) are coordinate-transformed, as the X-direction, Y-direction, and Z-direction positions of the bed, the i-axis rotation angle (relative isocentric rotation), the p-axis rotation angle (pitching rotation), the r-axis rotation angle (rolling rotation), and the diseased-site position of a patient; the respective axes of the bed capture these transformed data items, as input position data items, and the respective axes are driven so that the patient diseased site is moved to a desirable position.

However, in the case where, while the diseased site or the like is being monitored by an X-ray image-capturing device, the i-axis, the p-axis, and the r-axis are adjusted, it is normally impossible to dispose the diseased site in such a way as to pass through the rotation center of each axis; therefore, the diseased site moves in the X-axis direction, Y-axis direction, or Z-axis direction, or in a direction obtained by combining these directions. As a result, in some cases, the diseased site falls outside the image capturing area of the X-ray image-capturing device; thus, in order to prevent the diseased site from falling outside the image capturing area, it is required to subtly adjust the X-axis, the Y-axis, and the Z-axis so that the position of the diseased site does not move.

In a conventional radiation-therapy bed system, there is provided six degrees of freedom in the driving axes, and by driving each axis, the diseased site of a patient can be moved to a desirable position; however, in the practical positioning work for the diseased site, it is required to subtly adjust the X-axis, the Y-axis, and the Z-axis, as described above. Therefore, there has been a problem that this adjustment work is extremely bothersome to the engineer or the like, and because the positioning work takes a long time, the throughput of the particle beam therapy system cannot be improved.

SUMMARY OF THE INVENTION

The objective of the present invention is to obtain a driving type patient platform in which there can efficiently be performed the positioning work for making the position and the posture of a diseased site coincide with those established when a treatment plan is generated.

There are provided translation unit that translate the top board in the X direction, the Y direction, and the Z direction, respectively, in a fixed coordinate system fixed to an installation place; rotation unit that rotate the top board in the $\theta$ direction around the X axis, the $\phi$ direction around the Y axis, and the $\xi$ direction around the Z axis, respectively; and a control device that controls the translation unit and the rotation unit, based on an inputted desired rotation center point and an inputted desired rotation angle. The control device is provided with a rotation drive signal generation unit that generates a rotation drive signal for performing rotation movement of the top board from the reference position states of the translation unit and the rotation unit to the desired rotation angle; and a translation drive signal generation unit that generates a translation drive signal for translating the translation unit in such a way that the amount of translation movement, of the desired rotation center point, that is caused by the rotation movement becomes the same as or smaller than a predetermined value.

Based on an inputted desired rotation center point and an inputted desired rotation angle, a driving type patient platform according to the present invention is driven by combining the rotation drive of the top board and the translation drive performed in such a way that the translation movement amount, of the desired rotation center point, that is produced by rotation-moving the top board to the desired rotation angle is the same as or smaller than a predetermined value, so that the patient platform can automatically be rotated on a point within a predetermined distance from the desired rotation center point; therefore, there can efficiently be performed the positioning work for making the position and the posture of a diseased site coincide with those established when a treatment plan is generated.

The foregoing and other object, features, aspects, and advantages of the present invention will become more apparent from the following detailed description of the present invention when taken in conjunction with the accompanying drawings.

BRIEF DESCRIPTION OF THE DRAWINGS

FIG. 4A is an orthographic three-view for representing a coordinate system in the case where the patient platform in FIG. 1 is a control subject;

FIG. 6A is an orthographic three-view obtained by adding a coordinate system for a pitching rotation member to FIG. 5A and FIG. 5B;

FIG. 7 is a flowchart representing a program according to Embodiment 1 or 2;

A set of FIG. 8A

A set of FIG. 10A

A set of FIG. 13A

A set of FIG. 14A

DETAILED DESCRIPTION OF THE PREFERRED EMBODIMENTS

Embodiment 1

Figure 1:
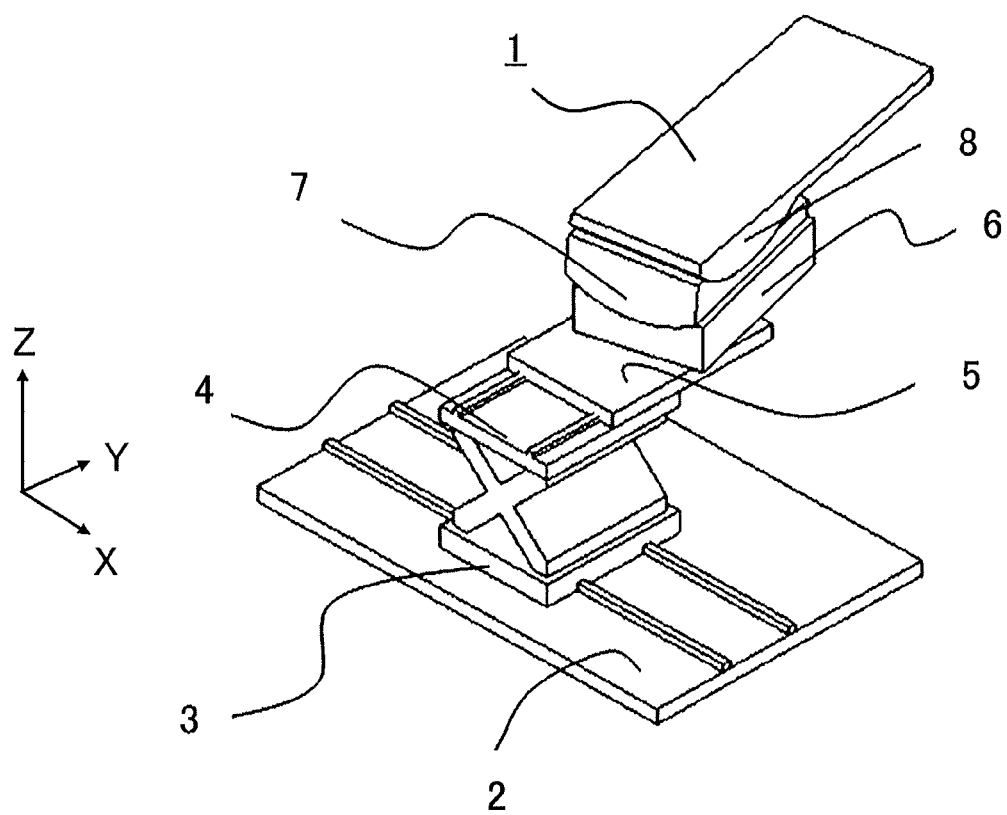
FIG. 1 is a schematic configuration diagram illustrating a driving type patient platform (patient platform) according to Embodiment 1 or 2 of the present invention.

FIG. 1 is a schematic configuration diagram illustrating a driving type patient platform (patient platform) according to Embodiment 1 of the present invention. Based on FIG. 1, the configuration of the patient platform, which is a control subject, will be explained. A driving type patient platform (bed type) 1 is an example of control subject in Embodiment 1. The driving type patient platform 1 is installed on a floor 2. A patient platform configuration member (X-translation member) 3 is one of members configuring the patient platform and is driven in the X direction with respect to the floor 2. A patient platform configuration member (Z-translation member) 4 is one of members configuring the patient platform and is driven in the Z direction with respect to the X-translation member 3. A patient platform configuration member (Y-translation member) 5 is one of members configuring the patient platform and is driven in the Y direction with respect to the Z-translation member 4. A patient platform configuration member (yaw rotation member) 6 is one of members configuring the patient platform and is driven in a yaw rotation manner with respect to the Y-translation member 5. A patient platform configuration member (rolling rotation member) 7 is one of members configuring the patient platform and is driven in a rolling rotation manner with respect to the yaw rotation member 6. A patient platform configuration member (pitching rotation member) 8 is one of members configuring the patient platform and is driven in a pitching rotation manner with respect to the rolling rotation member 7. The X-translation member 3, the Z-translation member 4, and the Y-translation member 5 are translation unit. The yaw rotation member 6, the rolling rotation member 7, and the pitching rotation member 8 are rotation unit. The patient platform configuration members 3 to 8 are driven by a driving device (unillustrated), based on a control signal from a control device 29 (unillustrated).

Figure 2A:
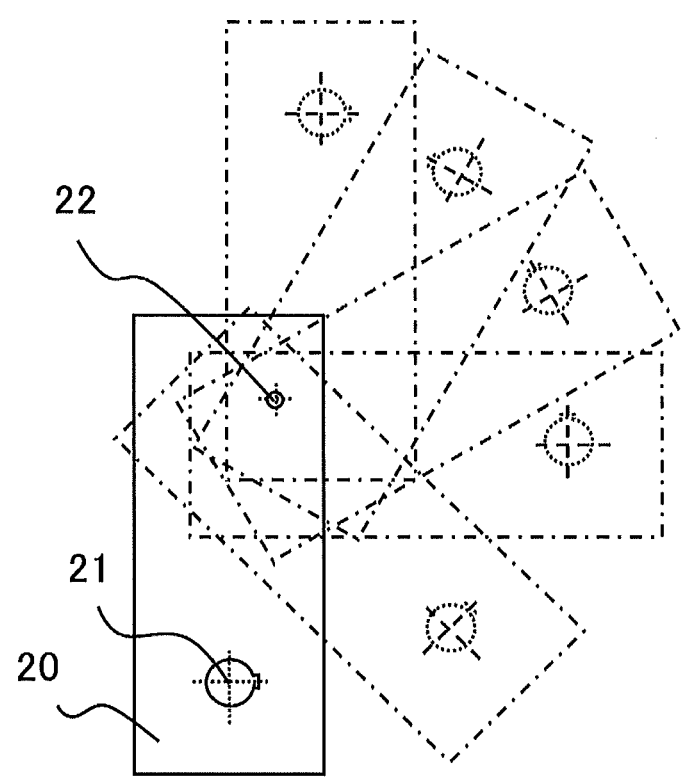
FIG. 2A and FIG. 2B are charts for explaining that a driving subject is rotation-driven on a desired position.
Figure 2B:
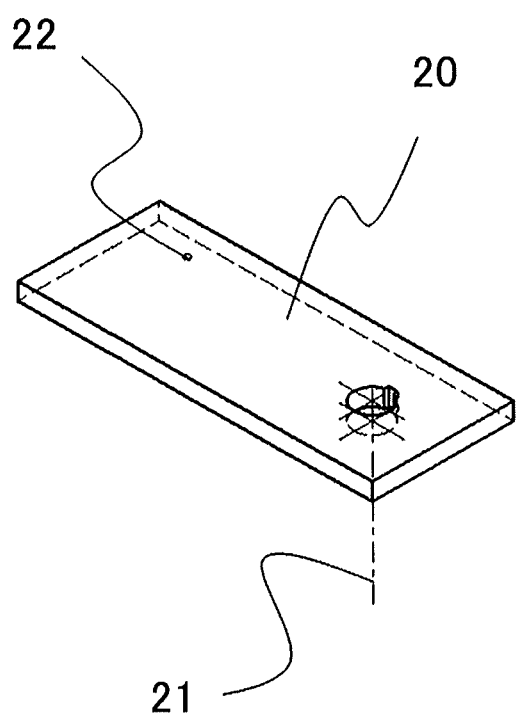

Next, based on FIG. 2A and FIG. 2B, there will be explained the operation of "rotation-driving a rotation subject with respect to a desired position", which is implemented in the present invention. FIG. 2A and FIG. 2B are charts for explaining a method of realizing the operation of rotation-driving a driving subject with respect to a desired position. FIG. 2A is a plan view; FIG. 2B is a bird's eye view. A driving subject 20 signifies a driving subject such as the top board of a patient platform. A rotation drive center (axis) 21 signifies a rotation drive center (axis) in the case where the driving subject 20 is rotation-driven by a rotation driving device such as a motor. A desired position 22 is a point (desired rotation center point) for expressing a desired position as an imaginary rotation center such as an isocenter, which is an irradiation reference.

FIG. 2A and FIG. 2B illustrates that the driving subject 20, which is a rigid body, is rotated on the rotation drive center (axis) 21 and is concurrently moved in a translation manner so that the imaginary rotation center becomes the desired position 22. In Embodiment 1, rotation driving and translation driving are combined in such a way as described above so that the driving subject is moved in a rotation manner at the desired position.

Figure 3:
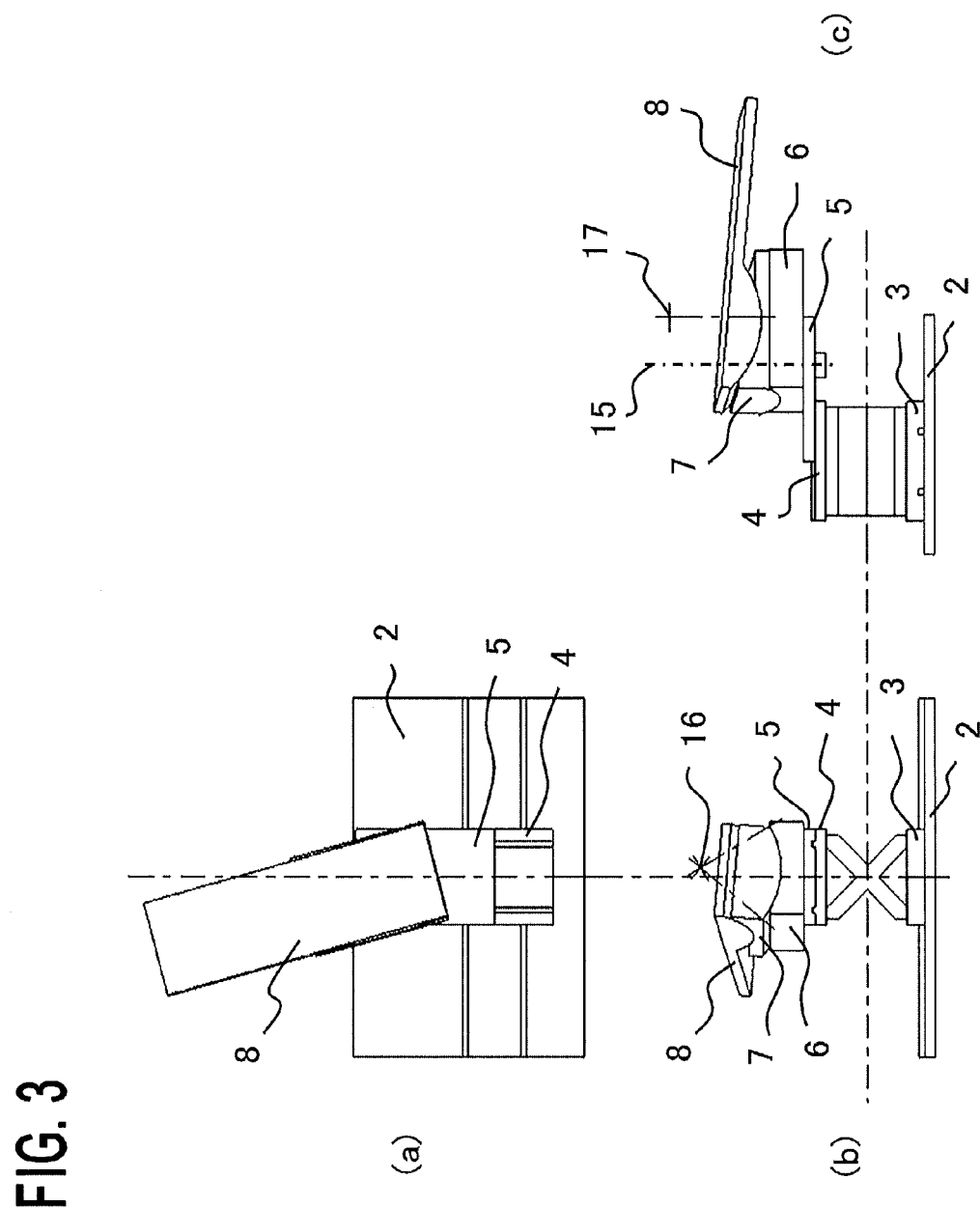
FIG. 3 is an orthographic three-view of the patient platform in FIG. 1.

FIG. 3 is an orthographic three-view of a patient platform according to Embodiment 1. FIG. 3(a) is a plan view of the patient platform 1; FIG. 3(b) is an elevation view of the patient platform 1; FIG. 3(c) is a side view of the patient platform 1. The yaw rotation member 6 is driven in a yaw rotation manner on a yaw rotation center (axis) 15 with respect to the Y-translation member 5. The rolling rotation member 7 is driven in a rolling rotation manner on a rolling rotation center (axis) 16 with respect to the yaw rotation member 6. The pitching rotation member 8 is driven in a pitching rotation manner on a pitching rotation center 17 with respect to the rolling rotation member 7.

Figure 4B:
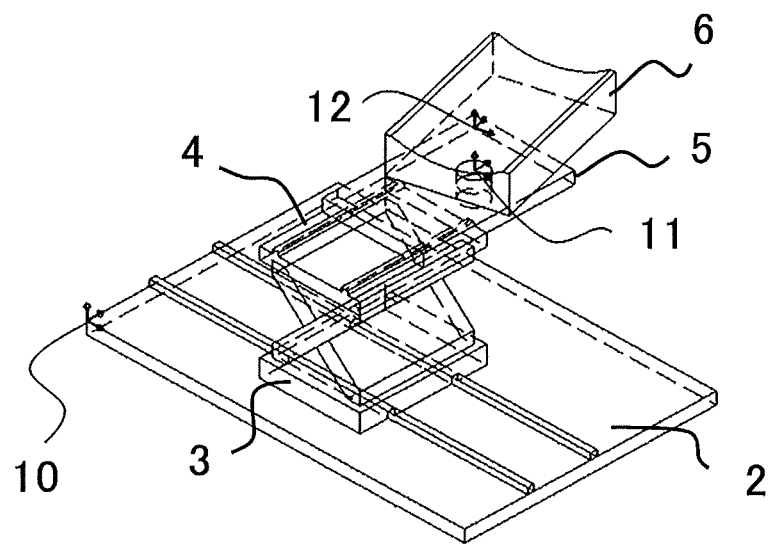
FIG. 4B is a schematic configuration diagram for representing a coordinate system in the case where the patient platform in FIG. 1 is a control subject.
Figure 5A:
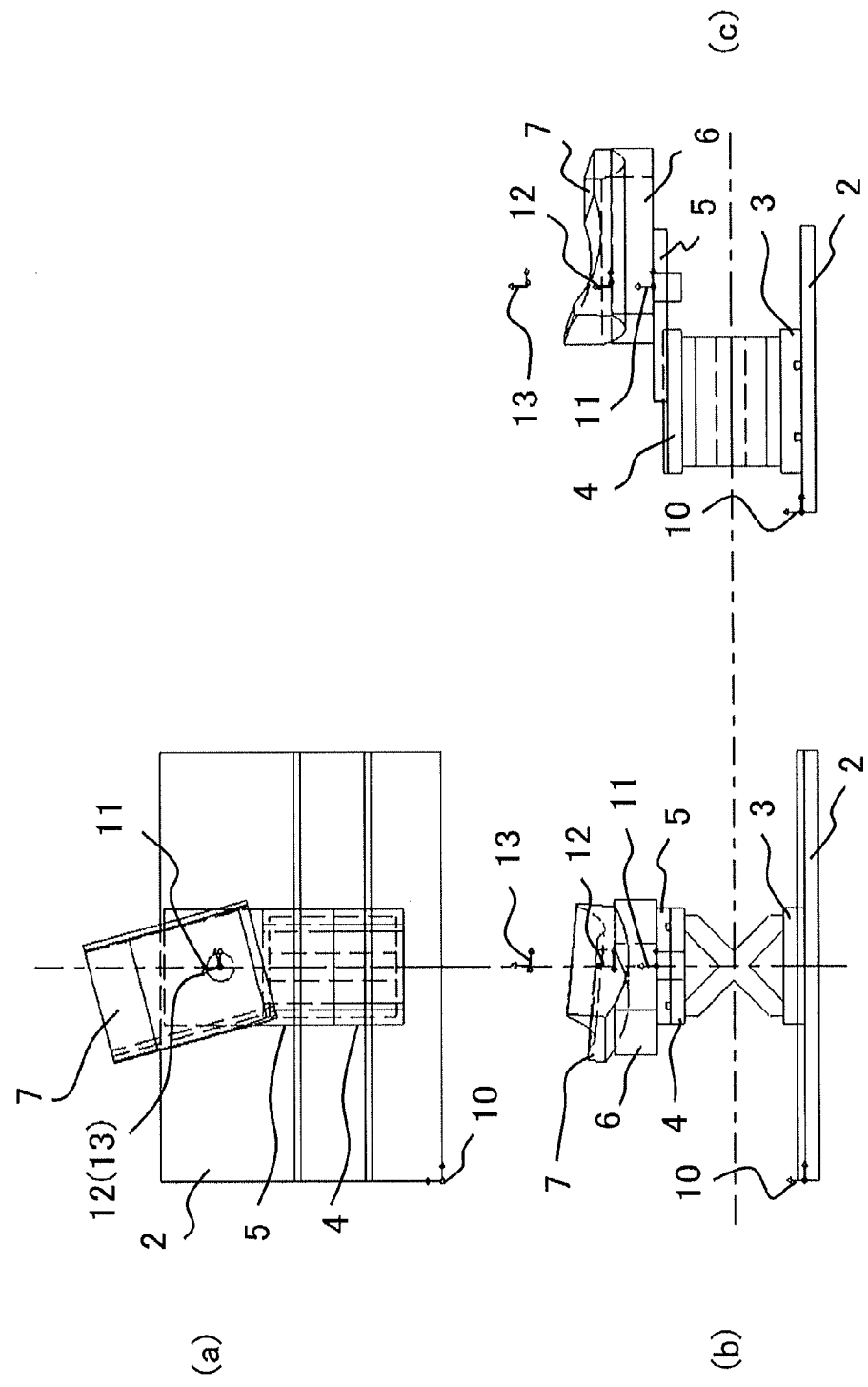
FIG. 5A is an orthographic three-view obtained by adding a coordinate system for a rolling rotation member to FIG. 4A and FIG. 4B.
Figure 5B:
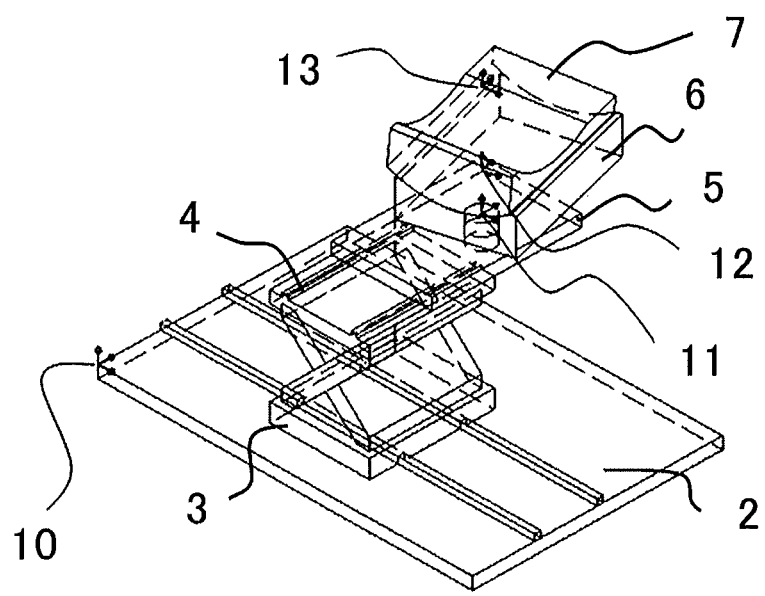
FIG. 5B is a schematic configuration diagram obtained by adding a coordinate system for a rolling rotation member to FIG. 4A and FIG. 4B.
Figure 6B:
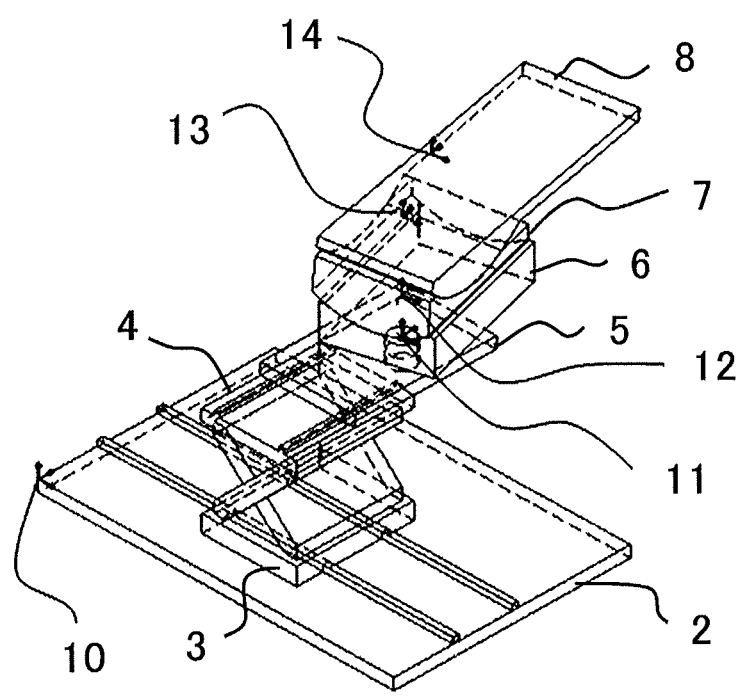
FIG. 6B is a schematic configuration diagram obtained by adding a coordinate system for a pitching rotation member to FIG. 5A and FIG. 5B.

Each of FIGS. 4A through 6A is an orthographic three-view for representing a coordinate system in the case where the patient platform 1 in FIG. 1 is a control subject in Embodiment 1. FIG. 4A is an orthographic three-view for representing a coordinate system in the case where the patient platform is a control subject; FIG. 4B is a schematic configuration diagram for representing a coordinate system in the case where the patient platform in FIG. 1 is a control subject; FIG. 5A is an orthographic three-view obtained by adding a coordinate system for a rolling rotation member to FIG. 4A and FIG. 4B; FIG. 6A is an orthographic three-view obtained by adding a coordinate system for a pitching rotation member to FIG. 5A and FIG. 5B; FIG. 6B is a schematic configuration diagram obtained by adding a coordinate system for a pitching rotation member to FIG. 5A and FIG. 5B. Each of FIGS. 4A(a), 5A(a), and 6A(a) is a plan view of the patient platform 1; Each of FIGS. 4A(b), 5A(b), and 6A(b) is an elevation view of the patient platform 1; Each of FIGS. 4A(c), 5A(c), and 6A(c) is a side view of the patient platform 1; Each of FIGS. 4B, 5B, and 6B is a bird's eye view of the patient platform 1. Based on FIGS. 4A through 6A and FIGS. 4B through 6B, the coordinate system in the present invention will be explained.

A coordinate system 10 is a coordinate system $O_{fix}$ (fixed coordinate system) fixed in a treatment room. A coordinate system 11 is a coordinate system $o_5$ fixed to the Y-translation member 5. The relationship between the coordinate system 10 and the coordinate system 11 is uniquely determined by the respective states of the X-translation member 3, the Z-translation member 4, and the Y-translation member 5, and the coordinate systems can be superimposed on each other through translation movement.

A coordinate system 12 is a coordinate system $o_6$ fixed to the yaw rotation member 6. The relationship between the coordinate system 11 and the coordinate system 12 is uniquely determined by the state of the yaw rotation member 6. When, as illustrated in FIG. 4A and FIG. 4B, the coordinate system 12 is disposed on the rotation axis of the yaw rotation, the direction vector from the origin of the coordinate system 11 to the origin of the coordinate system 12 is constant regardless of the state of the yaw rotation member 6; thus, the coordinate systems can be superimposed on each other through translation movement and yaw rotation.

A coordinate system 13 is a coordinate system $o_7$ fixed to the rolling rotation member 7. The relationship between the coordinate system 12 and the coordinate system 13 is uniquely determined by the state of the rolling rotation member 7. When, as illustrated in FIG. 5A and FIG. 5B, the coordinate system 13 is disposed on the rotation axis of the rolling rotation, the direction vector from the origin of the coordinate system 12 to the origin of the coordinate system 13 is constant regardless of the state of the rolling rotation member 7; thus, the coordinate systems can be superimposed on each other through translation movement and rolling rotation.

A coordinate system 14 is a coordinate system $o_{obj}$ (moving coordinate system) fixed to the pitching rotation member 8 (top board). The relationship between the coordinate system 13 and the coordinate system 14 is uniquely determined by the state of the pitching rotation member 8. When, as illustrated in FIG. 6A and FIG. 6B, the coordinate system 14 is disposed on the rotation axis of the pitching rotation, the direction vector from the origin of the coordinate system 13 to the origin of the coordinate system 14 is constant regardless of the state of the pitching rotation member 8; thus, the coordinate systems can be superimposed on each other through translation movement and pitching rotation.

FIG. 7 is a flowchart representing a program according to Embodiment 1; this program is installed in the control device 29. Based on FIG. 7, the flow of the program will be explained.

In the step S1, initialization is implemented. In the step S1, declaration and definition of variables are performed. In the step S2, reading is implemented. In the step S2, when the state of the patient platform is a state "a" (reference state), there is read data that specifies the respective positions and postures of the patient platform configuration members 3 through 8. In the step S3, reading is implemented. In the step S3, there is read the coordinates $P_{fix}$ (X, Y, Z) of a desired imaginary rotation center point (desired rotation center point) P such as an isocenter which is an irradiation reference.

In the step S4, calculation is implemented. In the step S4, when the patient platform is in the state "a", the foregoing desired point $P_{fix}$ (X, Y, Z) in the fixed coordinate system $O_{fix}$ is coordinate-transformed into coordinates $p_a$ (x, y, z) in a "coordinate system $o_{obj}$ fixed to the top board". In the step S5, reading is implemented. In the step S5, when the state of the patient platform is a state "b", there is read data that specifies the respective positions and postures of the patient platform configuration members 3 through 8. The reading of the data corresponds to reading of a desired rotation angle. In the step S6, calculation is implemented. In the step S6, assuming that the patient platform being fixed to the top board has come into the state "b" the coordinates $p_a$ (x, y, in the "coordinate system $o_{obj}$ fixed to the top board" is coordinate-transformed into the coordinates $P_{ab}$ (X, Y, Z) in the "coordinate system $O_{fix}$ fixed in the treatment room".

The step S7 is a difference calculation step where a difference is calculated. In the step S7, there is calculated the difference between the $P_{fix}$ (X, Y, Z) read in the step S3 and the $P_{ab}$ (X, Y, Z) obtained in the step S6. The step S8 is an outputting step where outputting is implemented. In the step S8, there is outputted the difference "$P_{ab}$ (X, Y, Z)–$P_{fix}$ (X, Y, Z)" calculated in the step S7.

The control device 29 is provided with a rotation drive signal generation unit that generates a rotation drive signal for a rotation unit for rotating the patient platform from the state "a" to the state "b", based on the state "a" of the patient platform that has not been driven in a rotating manner and the state "b", of the patient platform, which is a driving target (desired posture), i.e., based on a desired rotation angle at a time when the patient platform is rotated from the state "a" to the state "b"; and a translation drive signal generation unit that generates a translation drive signal for compensating the calculated difference "$P_{ab}$ (X, Y, Z)–$P_{fix}$ (X, Y, Z)" and translating the translation unit. The control device 29 generates the rotation drive signal and the translation drive signal. With regard to the details thereof, the contents of each step will be described below.

In the step S1, initialization is implemented; the details thereof will be described below. In the step S1, there are implemented declaration of variables required by the program described in Embodiment 1 and definition of parameters and the like that represent geometric information on a patient platform. The variables required by the program are, for example, what (referred to as "the state of a patient platform", hereinafter) specify the position and the posture of the patient platform 1, the coordinates of a desired imaginary rotation center point, a rotation matrix (a primary transformation matrix), and the like. The parameters that represent geometric information on the patient platform 1 denote the position vectors representing the positions of the origins of the coordinate systems 11 through 14 at a time when all the drive apparatuses for the patient platform 1 are at the reference positions, i.e., at a time when all the patient platform configuration members 3 through 8 are at the reference positions (referred to as "the state of the reference position", hereinafter).

The state of the patient platform 1 is represented as $\{x_s, y_s, z_s, \theta_s, \phi_s, \xi_s\}$. In this regard, however, $\{x_s, y_s, z_s, \theta_s, \phi_s, \xi_s\}$ are specified as follows.

The character $x_s$ is the x-direction displacement of the X-translation member 3 with respect to the reference position on the floor 2.

The character $y_s$ is the y-direction displacement of the Y-translation member 5 with respect to the reference position on the Z-translation member 4.

The character $z_s$ is the z-direction displacement of the Z-translation member 4 with respect to the reference position on the X-translation member 3.

The character $\theta_s$ is the pitching-rotation-direction displacement angle of the pitching rotation member 8 with respect to the reference position on the rolling rotation member 7.

The character $\phi_s$ is the rolling-rotation-direction displacement angle of the rolling rotation member 7 with respect to the reference position on the yaw rotation member 6.

The character $\xi_s$ is the yaw-rotation-direction displacement angle of the yaw rotation member 6 with respect to the reference position on the Y-translation member 5.

The coordinates of the desired imaginary rotation center point P is represented as $P_{fix}$ (X, Y, Z). The rotation matrixes for pitching rotation, rolling rotation, and yaw rotation are represented as the equations (1) through (3), respectively.

$$R_x(\theta) = \begin{bmatrix} 1 & 0 & 0 \\ 0 & \cos\theta & -\sin\theta \\ 0 & \sin\theta & \cos\theta \end{bmatrix} \quad (1)$$

$$R_y(\phi) = \begin{bmatrix} \cos\phi & 0 & \sin\phi \\ 0 & 1 & 0 \\ -\sin\phi & 0 & \cos\phi \end{bmatrix} \quad (2)$$

$$R_z(\xi) = \begin{bmatrix} \cos\xi & -\sin\xi & 0 \\ \sin\xi & \cos\xi & 0 \\ 0 & 0 & 1 \end{bmatrix} \quad (3)$$

The parameters that represent geometric information on the patient platform in the state of the reference position are vectors that specify the positions of the origins of the coordinate systems 11 through 14, and are expressed as the equations (4) through (7).

$$(o_5 - O_{fix}) = \begin{bmatrix} X_5 \\ Y_5 \\ Z_5 \end{bmatrix} \quad (4)$$

where $(o_5 - O_{fix})$ is the position of the origin of the coordinate system 11 viewed from the fixed coordinate system.

$$(o_6 - O_{fix}) = \begin{bmatrix} X_6 \\ Y_6 \\ Z_6 \end{bmatrix} \quad (5)$$

where $(o_6 - O_{fix})$ is the position of the origin of the coordinate system 12 viewed from the fixed coordinate system.

$$(o_7 - O_{fix}) = \begin{bmatrix} X_7 \\ Y_7 \\ Z_7 \end{bmatrix} \quad (6)$$

where $(o_7 - O_{fix})$ is the position of the origin of the coordinate system 13 viewed from the fixed coordinate system.

$$(o_{obj} - O_{fix}) = \begin{bmatrix} X_{obj} \\ Y_{obj} \\ Z_{obj} \end{bmatrix} \quad (7)$$

where $(o_{obj} - O_{fix})$ is the position of the origin of the coordinate system 14 viewed from the fixed coordinate system.

In the step S2, reading is implemented; the details thereof will be described below. In the step S2, when the state of the patient platform is the state "a", there is read data that specifies the respective positions and postures of the patient platform configuration members 3 through 8. The state "a" denotes the state of the patient platform at a time when the desired rotation center point P is set. The variables that specify the state of the patient platform are as described in the detail of the step S1; thus, specific values are substituted for the variables. The state "a" of the patient platform 1 is represented as $\{x_a, y_a, z_a, \theta_a, \phi_a, \xi_a\}$.

In the step S3, reading is implemented; the details thereof will be described below. In the step S3, there is read the coordinates $P_{fix}$ (X, Y, Z) of a desired imaginary rotation center point P such as an isocenter which is an irradiation reference. In general, the coordinates $P_{fix}$ (X, Y, Z) of the desired imaginary rotation center point P is constant during a certain series of work; therefore, only when required to be changed, the coordinates $P_{fix}$ (X, Y, Z) is read and overwritten on the earlier one.

In the step S4, calculation is implemented; the details thereof will be described below. In the step S4, when the patient platform is in the state "a", the foregoing desired point $P_{fix}$ (X, Y, Z) in the fixed coordinate system $O_{fix}$ is coordinate-transformed into coordinates $p_a$ (x, y, z) in a "coordinate system $o_{obj}$ fixed to the top board".

At first, based on FIG. 4A and FIG. 4B, the relationship between the coordinate system 10 and the coordinate system 11 will be explained. As described in the detail of the step S1, in the state of the reference position, the coordinates of the origin of the coordinate system 11 is represented as the equation (4) as viewed from the fixed coordinate system (i.e., the coordinate system 10). In this situation, the patient platform is in the state "a"; thus, the coordinates of the origin of the coordinate system 11 is represented as follows, as viewed from the fixed coordinate system (i.e., the coordinate system 10).

$$(o_5 - O_{fix})|_{state\ a} = \begin{bmatrix} X_5 \\ Y_5 \\ Z_5 \end{bmatrix} + \begin{bmatrix} x_a \\ y_a \\ z_a \end{bmatrix} \quad (8)$$

In other words, when returned to the negative direction by the foregoing direction vector, the coordinate system 11 is superimposed on the coordinate system 10. Accordingly, the coordinate transformation from the coordinate system 11 into the fixed coordinate system (i.e., the fixed coordinate system 10) can be obtained by the following equation.

$$Q_{fix} = (o_5 - O_{fix})|_{state\ a} + q_5 \quad (9)$$

$$= \begin{bmatrix} X_5 \\ Y_5 \\ Z_5 \end{bmatrix} + \begin{bmatrix} x_a \\ y_a \\ z_a \end{bmatrix} + q_5$$

In this regard, however, $Q_{fix}$ is an arbitrary point q represented by the fixed coordinate system. In addition, $q_5$ is the arbitrary point q represented by the coordinate system 11 fixed to the Y-translation member 5.

Next, based on FIG. 4A and FIG. 4B, the relationship between the coordinate system 11 and the coordinate system 12 will be explained. The arbitrary point q viewed from the coordinate system 12 coincides with the point q viewed from the coordinate system 11 when, at first, translation movement is performed from the origin of the coordinate system 11 to the origin of the coordinate system 12 and then there is performed yaw rotation by ξ, which is the displacement angle of the coordinate system 12 with respect to the coordinate system 11. That is to say, the relationship is represented by the following equation.

$$q_5 = \begin{bmatrix} X_6 - X_5 \\ Y_6 - Y_5 \\ Z_6 - Z_5 \end{bmatrix} + R_z(\xi) q_6 \quad (10)$$

In this regard, however, $q_6$ is the arbitrary point q represented by the coordinate system 12 fixed to the yaw rotation member 6.

Similarly, based on FIG. 5A and FIG. 5B, the relationship between the coordinate system 12 and the coordinate system 13 will be explained. The arbitrary point q viewed from the coordinate system 13 coincides with the point q viewed from the coordinate system 12 when, at first, translation movement is performed from the origin of the coordinate system 12 to the origin of the coordinate system 13 and then there is performed rolling rotation by φ, which is the displacement angle of the coordinate system 13 with respect to the coordinate system 12. That is to say, the relationship is represented by the following equation.

$$q_6 = \begin{bmatrix} X_7 - X_6 \\ Y_7 - Y_6 \\ Z_7 - Z_6 \end{bmatrix} + R_y(\phi) q_7 \quad (11)$$

In this regard, however, $q_7$ is the arbitrary point q represented by the coordinate system 13 fixed to the rolling rotation member 7.

In the last place, based on FIG. 6A and FIG. 6B, the relationship between the coordinate system 13 and the coordinate system 14 will be explained. The arbitrary point q viewed from the coordinate system 14 coincides with the point q viewed from the coordinate system 13 when, at first, translation movement is performed from the origin of the coordinate system 13 to the origin of the coordinate system 14 and then there is performed pitching rotation by θ, which is the displacement angle of the coordinate system 14 with respect to the coordinate system 13. That is to say, the relationship is represented by the following equation.

$$q_7 = \begin{bmatrix} X_{obj} - X_7 \\ Y_{obj} - Y_7 \\ Z_{obj} - Z_7 \end{bmatrix} + R_x(\theta) q_{obj} \quad (12)$$

In this regard, however, $q_{obj}$ is the arbitrary point q represented by the coordinate system 14 fixed to the pitching rotation member 8 (top board).

By rearranging the equations (9) through (12), there can be performed coordinate transformation from "the coordinate system $o_{obj}$ fixed to the top board" into "the coordinate system $O_{fix}$ fixed to the treatment room", when the patient platform is in the state "a". As a result, the equation (13) is obtained.

$$Q_{fix} = \begin{bmatrix} x_a \\ y_a \\ z_a \end{bmatrix} + \begin{bmatrix} X_6 \\ Y_6 \\ Z_6 \end{bmatrix} + \quad (13)$$

$$R_z(\xi) \left\{ \begin{bmatrix} X_7 - X_6 \\ Y_7 - Y_6 \\ Z_7 - Z_6 \end{bmatrix} + R_y(\phi) \left( \begin{bmatrix} X_{obj} - X_7 \\ Y_{obj} - Y_7 \\ Z_{obj} - Z_7 \end{bmatrix} + R_x(\theta) q_{obj} \right) \right\}$$

The equation (13) is a coordinate transformation unit C2 (a second coordinate transformation unit) for performing transformation of the coordinate system from "the coordinate system $o_{obj}$ fixed to the top board" (moving coordinate system) into "the coordinate system $O_{fix}$ fixed to the treatment room" (fixed coordinate system).

By modifying the equation (13), there can be obtained coordinate transformation from "the coordinate system $O_{fix}$ fixed to the treatment room" (fixed coordinate system) into "the coordinate system $o_{obj}$ fixed to the top board" (moving coordinate system).

$$q_{obj} = R_x(\theta)^{-1} \left\{ R_y(\phi)^{-1} \left\{ R_z(\xi)^{-1} \left( Q_{fix} - \begin{bmatrix} x_a \\ y_a \\ z_a \end{bmatrix} - \begin{bmatrix} X_6 \\ Y_6 \\ Z_6 \end{bmatrix} \right) - \begin{bmatrix} X_7 - X_6 \\ Y_7 - Y_6 \\ Z_7 - Z_6 \end{bmatrix} \right\} - \begin{bmatrix} X_{obj} - X_7 \\ Y_{obj} - Y_7 \\ Z_{obj} - Z_7 \end{bmatrix} \right\} \quad (14)$$

$$= R_x(-\theta) \left\{ R_y(-\phi) \left\{ R_z(-\xi) \left( Q_{fix} - \begin{bmatrix} x_a \\ y_a \\ z_a \end{bmatrix} - \begin{bmatrix} X_6 \\ Y_6 \\ Z_6 \end{bmatrix} \right) - \begin{bmatrix} X_7 - X_6 \\ Y_7 - Y_6 \\ Z_7 - Z_6 \end{bmatrix} \right\} - \begin{bmatrix} X_{obj} - X_7 \\ Y_{obj} - Y_7 \\ Z_{obj} - Z_7 \end{bmatrix} \right\}$$

The equation (14) is a coordinate transformation unit C1 (a first coordinate transformation unit) for performing transformation of the coordinate system from "the coordinate system $O_{fix}$ fixed to the treatment room" (fixed coordinate system) into "the coordinate system $o_{obj}$ fixed to the top board" (moving coordinate system).

Accordingly, in the step S4, by utilizing the coordinate transformation unit C1, the foregoing desired point $P_{fix}$ (X, Y, Z) in the fixed coordinate system $O_{fix}$ at a time when the patient platform 1 is in the state "a" is coordinate-transformed into coordinates $p_a$ (x, y, z) in a "coordinate system $o_{obj}$ fixed to the top board". Specifically, in the equation (14), $p_a$ is substituted for $q_{obj}$, which is the arbitrary point q represented by the coordinate system 14 fixed to the pitching rotation member 8, the desired point $P_{fix}$ is substituted for $Q_{fix}$, which is the arbitrary point q represented by the fixed coordinate system, and $\theta_a$, $\phi_a$, and $\xi_a$, which are displacement angles at a time when the patient platform is in the state "a", are substituted for the displacement angles $\theta$, $\phi$, and $\xi$. In the step S4, the equation (15) is obtained.

$$p_a = R_x(-\theta_a)\left\{R_y(-\phi_a)\left\{R_z(-\xi_a)\left(P_{fix} - \begin{bmatrix} x_a \\ y_a \\ z_a \end{bmatrix} - \begin{bmatrix} X_6 \\ Y_6 \\ Z_6 \end{bmatrix}\right) - \begin{bmatrix} X_7 - X_6 \\ Y_7 - Y_6 \\ Z_7 - Z_6 \end{bmatrix}\right\} - \begin{bmatrix} X_{obj} - X_7 \\ Y_{obj} - Y_7 \\ Z_{obj} - Z_7 \end{bmatrix}\right\} \quad (15)$$

In the step S5, reading is implemented; the details thereof will be described below. In the step S5, when the patient platform 1 is in the state "b", there is read data that specifies the respective positions and postures of the patient platform configuration members 3 through 8. The state "b" denotes, for example, the target posture of the patient platform 1 to be achieved. The desired rotation angle is given as the angle of the state "b", i.e., as an absolute angle. The translation position of the patient platform 1 is uniquely determined in such a way as to be the desired imaginary rotation center point; thus, in the step S5, any value may be substituted. For the sake of simplicity, the value at a time when the patient platform 1 is in the state "a" is left as it is.

The state "b" of the patient platform 1 is represented as $\{x_a, y_a, z_a, \theta_b, \phi_b, \xi_b\}$.

In the step S6, calculation is implemented; the details thereof will be described below. In the step S6, assuming that the patient platform 1 being fixed to the top board 8 has come into the state "b", the coordinates $p_a$ (x, y, z) in the "coordinate system $o_{obj}$ fixed to the top board" is coordinate-transformed into the coordinates $P_{ab}$ (X, Y, Z) in the "coordinate system $O_{fix}$ fixed in the treatment room". Specifically, in the step S6, assuming that the patient platform 1 being fixed to the top board 8 has come into the state "b", the coordinates $p_a$ (x, Y, z) in the "coordinate system $o_{obj}$ fixed to the top board" is coordinate-transformed by use of the coordinate transformation unit C2 into the coordinates $P_{ab}$ (X, Y, Z) in the "coordinate system $O_{fix}$ fixed in the treatment room". In the step S6, the equation (16) is implemented.

$$P_{ab} = \begin{bmatrix} x_a \\ y_a \\ z_a \end{bmatrix} + \begin{bmatrix} X_6 \\ Y_6 \\ Z_6 \end{bmatrix} + R_z(\xi_b)\left\{\begin{bmatrix} X_7 - X_6 \\ Y_7 - Y_6 \\ Z_7 - Z_6 \end{bmatrix} + R_y(\phi_b)\left(\begin{bmatrix} X_{obj} - X_7 \\ Y_{obj} - Y_7 \\ Z_{obj} - Z_7 \end{bmatrix} + R_x(\theta_b)p_a\right)\right\} \quad (16)$$

The step S7 is a difference calculation step where a difference is calculated; the details thereof will be described below. In the step S7, there is calculated the difference between the $P_{fix}$ (X, Y, Z) read in the step S3 and the $P_{ab}$ (X, Y, Z) obtained in the step S6. In the step S7, the equation (17) is obtained.

$$\Delta P = P_{ab} - P_{fix} \quad (17)$$

The step S8 is an outputting step where outputting is implemented; the details thereof will be described below. In the step S8, $\Delta P$ ($=P_{ab}-P_{fix}$) calculated in the step S7 is outputted, as a compensation amount, to the respective controllers of the driving devices for the patient platform configuration members 3 through 5. This compensation amount becomes the translation drive signal. $\Delta P$ ($=P_{ab}-P_{fix}$) physically denotes the direction vector between the point P at a time when the patient platform 1 is in the state "a" and the point P at a time when the patient platform 1 is in the state "b", i.e., the vector amount obtained from the movement of the point P. Accordingly, by compensating the state "b" by $\Delta P$ ($=P_{ab}-P_{fix}$) calculated in the step S7, the rotation center can be the desired point P as the posture of the patient platform 1 is kept to be in the state "b". As a result, the compensated state "b'" of the patient platform 1 can be expressed as follows.

$$\{x_a - \Delta P_x, y_a - \Delta P_y, z_a - \Delta P_z, \theta_b, \phi_b, \xi_b\}$$

where $\Delta P_x$, $\Delta P_y$, and $\Delta P_z$ denote the x, y, and z components of $\Delta P$, respectively.

Figure 8A:
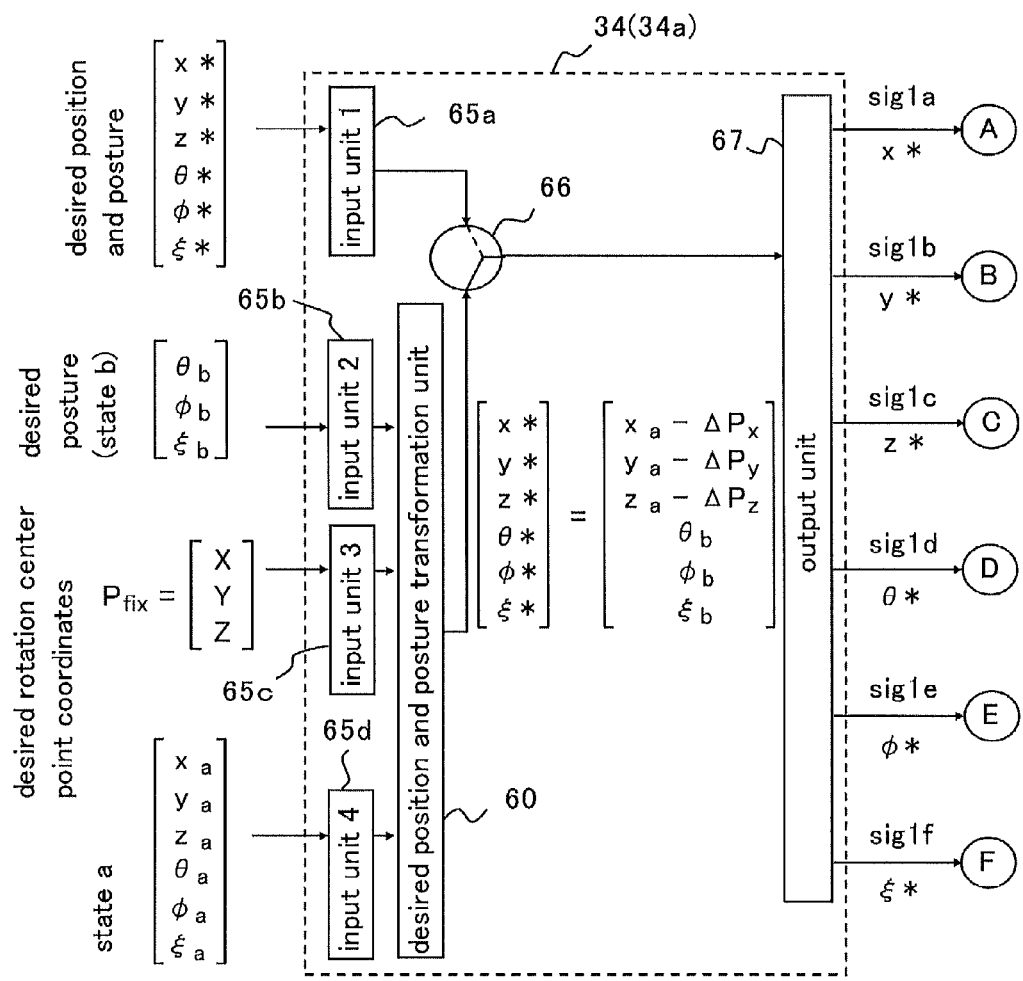
FIG. 8B is a block diagram for explaining the control of the patient platform according to Embodiment 1.
Figure 8B:
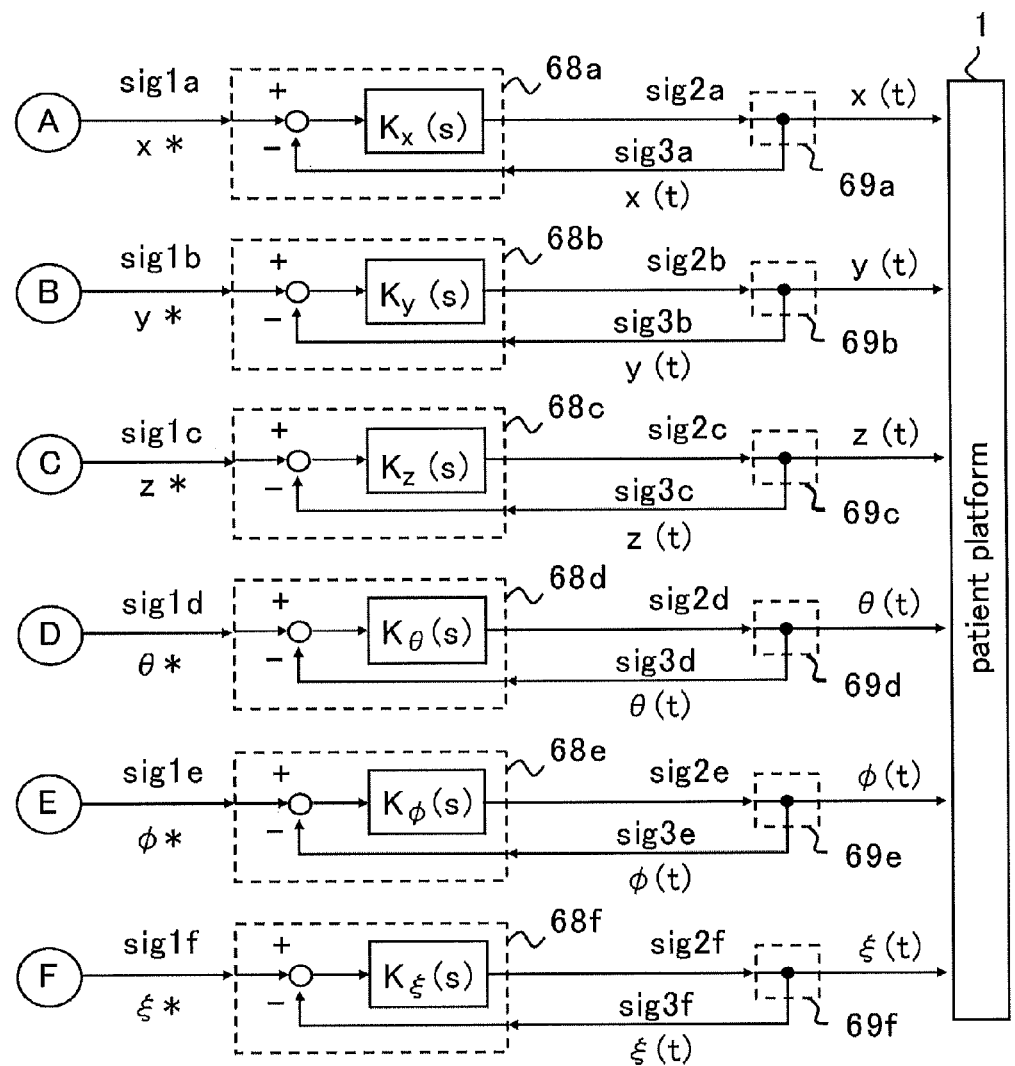
Figure 9:
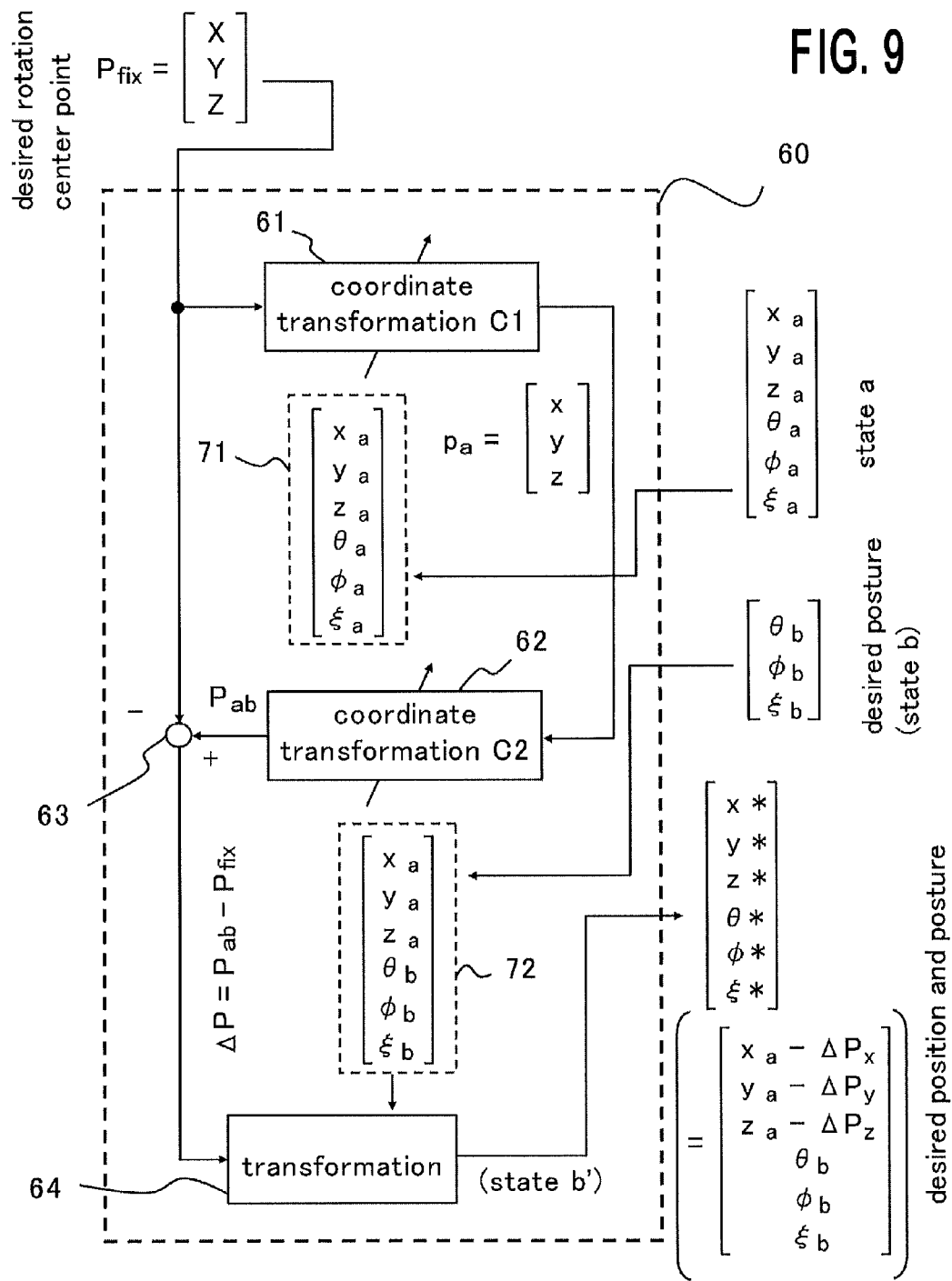
FIG. 9 is a block diagram illustrating a desired position and posture transformation unit in FIGS. 8A and 8B.

The program represented in the flowchart in FIG. 7 is integrated in a controller 34. The method in which the controller 34 controls the patient platform 1 will be explained. A set of FIG. 8A and FIG. 8B is a block diagram for explaining the control of the patient platform 1 according to Embodiment 1; FIG. 9 is a block diagram illustrating a desired position and posture transformation unit. The controller 34 (34a) has four input units 65a, 65b, 65c, and 65d, a desired position and posture transformation unit 60, a mode switch 66, and an output unit 67. The mode switch 66 performs switching between desired position and posture $\{x^*, y^*, z^*, \theta^*, \phi^*, \xi^*\}$ from the input unit 65a and desired position and posture $\{x^*, y^*, z^*, \theta^*, \phi^*, \xi^*\}$ from the desired position and posture transformation unit 60. In the case of the mode 1, a command signal is outputted to the driving device for the patient platform 1, based on the desired position and posture from the input unit 65a; in the case of the mode 2, a command signal is outputted to the driving device for the patient platform 1, based on the desired position and posture from the desired position and posture transformation unit 60. The mode 1 has been implemented to date; in the mode 2, the flowchart in FIG. 7 is implemented. The characters with "*" denotes target values that do not change with time, and so are the characters with "*'" among characters explained hereinafter.

The state "a" of the patient platform and the coordinates $P_{fix}$ (X, Y, Z) of the desired rotation center point read in the steps S2 and S3 are inputted to the input units 65d and 65c, respectively. As described above, the state "a" is the state of the patient platform 1 at a time when the coordinates $P_{fix}$ of the desired rotation center point is inputted. The target posture (the state "b") of the patient platform read in the steps S5 is inputted to the input unit 65b. The desired position and posture transformation unit 60 implements the steps S6 through S8 so as to calculate the desired position and posture (state "b'") $\{x_a - \Delta P_x, y_a - \Delta P_y, z_a - \Delta P_z, \theta_b, \phi_b, \xi_b\}$. Based on the compensated desired position and posture $\{x^*, y^*, z^*, \theta^*, \phi^*, \xi^*\}$ in the state "b'" of the patient platform 1, the output unit 67 outputs the command signals sig1a through sig1f to driving devices 35 through 40 (refer to FIG. 11) for six axes. A sensor, such as an encoder, for detecting the rotation angle is disposed in each of the driving devices (motors) 35 through 40. In FIGS. 8A and 8B, the motors and encoders for six axes are designated as motor/encoders 69*a* through 69*f*. In general, the driving devices 35 through 40 are controlled by drivers. The driving devices 35 through 40 are controlled in such a way that the driving devices (motors) 35 through 40 are driven by drive signals sig2*a* through sig2*f*; the present statuses x(t) through ξ(t) of the driving devices (motors) 35 through 40 are detected by encoders or the like, and detection signals sig3*a* through sig3*f* from the encoders or the like are fed back to motor drivers 68*a* through 68*f*.

The command signal sig1*a*, the drive signal sig2*a*, the detection signal sig3*a*, the present state x(t), the driver 68*a*, and the motor/encoder 69*a* are related to the driving device (X translation motor) 35. The command signal sig1*b*, the drive signal sig2*b*, the detection signal sig3*b*, the present state y(t), the driver 68*b*, and the motor/encoder 69*b* are related to the driving device (Y translation motor) 36. The command signal sig1*c*, the drive signal sig2*c*, the detection signal sig3*c*, the present state z(t), the driver 68*c*, and the motor/encoder 69*c* are related to the driving device (Z translation motor) 37. The command signal sig1*d*, the drive signal sig2*d*, the detection signal sig3*d*, the present state θ(t), the driver 68*d*, and the motor/encoder 69*d* are related to the driving device (yaw rotation motor) 38. The command signal sig1*e*, the drive signal sig2*e*, the detection signal sig3*e*, the present state ϕ(t), the driver 68*e*, and the motor/encoder 69*e* are related to the driving device (rolling rotation motor) 39. The command signal sig1*f*, the drive signal sig2*f*, the detection signal sig3*f*, the present state ξ(t), the driver 68*f*, and the motor/encoder 69*f* are related to the driving device (pitching rotation motor) 40.

The operation of the desired position and posture transformation unit 60 will be explained with reference to FIG. 9. The desired position and posture transformation unit 60 has the first coordinate transformation unit C1 (61), the second coordinate transformation unit C2 (62), a calculation unit 63, and a desired position and posture calculation unit 64. The first coordinate transformation unit C1 (61) implements the step S4. In the state "a" set by its program variables 71, the first coordinate transformation unit C1 (61) transforms the coordinates $P_{fix}$ (X, Y, Z) of the desired rotation center point in a fixed coordinate system into the coordinates $p_a$ (x, y, z) in a moving coordinate system.

The second coordinate transformation unit C2 (62) implements the step S6. Assuming that the state of the patient platform is in the state "b" (target position $\{x_a, y_a, z_a\}$, target posture $\{θ_b, ϕ_b, ξ_b\}$) set by its program variables 72, the second coordinate transformation unit C2 (62) transforms the coordinates $p_a$ (x, y, z) of the desired rotation center point in a moving coordinate system into the coordinates $P_{ab}$ (X, Y, Z) in a fixed coordinate system. The calculation unit 63 implements the step S7 so as to calculate ΔP (=$P_{ab}$−$P_{fix}$). The desired position and posture transformation unit 64 implements the step S8 so as to calculate the desired position and posture $\{x^*, y^*, z^*, θ^*, ϕ^*, ξ^*\}$ in the compensated state "b" of the patient platform 1, i.e., $\{x_a−ΔP_x, y_a−ΔP_y, z_a−ΔP_z, θ_b, ϕP_b, ξ_b\}$.

There are conceivable roughly three methods to provide the state "b". They are a regulator type, a servo system type, and a JOG drive type. The regulator type method provides the target posture to be eventually obtained. In this case, the state "b" does not change during a series of operations. The servo system type method instructs halfway passing points (postures) as well. In this case, the state "b" changes in accordance with a predetermined sequence. The JOG drive type method performs instruction through a JOG lever. In this case, the state "b" changes at a constant speed when the JOG lever is thrown. The JOG driving will be described in detail in Embodiment 3.

The patient platform 1 in Embodiment 1 can be rotated at a desired point, by combining rotation drive and translation drive in which there is compensated the difference between the coordinates of an arbitrary point (the desired point P) in the state "a" and the coordinates of an arbitrary point in the state "b", based on the desired point P (the desired rotation center point P) and the desired rotation angle. By only performing control inputting for implementing rotation drive, the patient platform 1 can be rotated on a desired point P; therefore, there can efficiently be performed the positioning work for making the position and the posture of a diseased site coincide with those established when a treatment plan is generated.

By utilizing the isocenter, which is the irradiation center of a particle beam therapy system, as the desired point P of the patient platform 1, the movement of the patient platform 1 can be made compact. Because the movement of the patient platform 1 becomes compact, the interference between the patient platform 1 or a patient fixed on the patient platform and apparatuses other than the patient platform 1 of the particle beam therapy system can more readily be prevented in the positioning work for making the position of the patient platform coincide with the position established in the treatment plan.

Regardless of the type of a patient platform such as a bed or a chair, the program, according to Embodiment 1, for implementing the positioning method for the patient platform 1 can be applied even to an already installed patient platform, without hardware modification or additional construction work being carried out. As described above, due to the scalability, there can be performed the control of diseased-site rotation on the desired point P; thus, there can readily be performed the positioning work where the position and the posture of a diseased site is made to coincide with those established when the treatment plan is generated. As a result, the time for preparing treatment can considerably be reduced.

The foregoing explanation has been made with an example where the desired rotation angle is given as the angle of the state "b", i.e., an absolute angle; however, it may also be allowed that the desired rotation angle is given as the relative angle between the state "a" and the state "b". In both cases, the posture of a diseased site can be made to coincide with the posture given by the desired rotation angle.

As described above, in the driving type patient platform 1 according to Embodiment 1, there are provided the translation unit 3, 4, and 5 that translate the top board 8 in the X direction, the Y direction, and the Z direction, respectively, in the fixed coordinate system 10 fixed to the installation place; the rotation unit 6, 7, and 8 that rotate the top board 8 in the θ direction around the X axis, the ϕ direction around the Y axis, and the ξ direction around the Z axis, respectively; and the control device that controls the translation unit 3, 4, and the rotation unit 6, 7, and 8, based on an inputted desired rotation center point P and an inputted desired rotation angle. The control device is provided with the rotation drive signal generation unit that generates the rotation drive signal for moving the top board 8 in a rotating manner from the reference state "a" of the translation unit 3, 4, and 5 and the rotation unit 6, 7, and 8 to a desired rotation angle; and the translation drive signal generation unit that generates the translation drive signal for translating the translation unit 3, 4, and 5 in such a way that there is compensated the amount of translation movement, of the desired rotation center point P, that is caused by the rotation movement. As a result, there can be performed the control of diseased-site rotation on the desired rotation center point P; therefore, there can efficiently be performed the positioning work for making the position and the posture of a diseased site coincide with those established when a treatment plan is generated.

Embodiment 2

In Embodiment 1, the foregoing explanation has been made with an example where there is performed the control of diseased-site rotation on the desired rotation center point P; however, even in the case where a diseased site is rotated within a predetermined distance from the desired rotation center point P, i.e., the diseased site is rotated at a desired rotation angle and the desired rotation center point P in the moving coordinate system is moved by as far as a predetermined distance, as viewed from the fixed coordinate system, there can efficiently be performed the positioning work for making the position and the posture of a diseased site coincide with those established when a treatment plan is generated. As described above, with regard to the positioning work for a diseased site, it is only necessary that, during the work, the diseased site is within the image capturing area of the X-ray image-capturing device; therefore, even in the case where the driving device for the patient platform 1 is controlled by the command signals sig1a through sig1f based on the desired position and posture $\{x^*, y^*, z^*, \theta^*, \phi^*, \xi^*\}$ in which there is set a positional deviation (coordinate deviation) or an offset due to the error in the driving device for the patient platform 1, by rotating the driving subject 20 (the top board 8) in such a way that the rotation position is within a predetermined distance from the desired rotation center point P, there can efficiently be performed the positioning work for making the position and the posture of a diseased site coincide with those established when a treatment plan is generated. The predetermined distance is the distance between the outer circumference of the image capturing area and the diseased site; the predetermined value of the translation movement amount is this predetermined distance.

In the case where the driving device is controlled by the command signals sig1a through sig1f with which an offset is set, the following effects are demonstrated. For example, in the case where a diseased site appears at the bottom of the captured image of the X-ray image-capturing device, by rotating the posture of the diseased site on the desired rotation center point P, the whole diseased site can be moved to the center of the captured image. In such a way as described above, it is made possible to move the diseased site to a desired position in a shorter time than that in the case where the diseased site is moved to the center of the captured image and then is rotated on the desired rotation center point P.

Figure 10A:
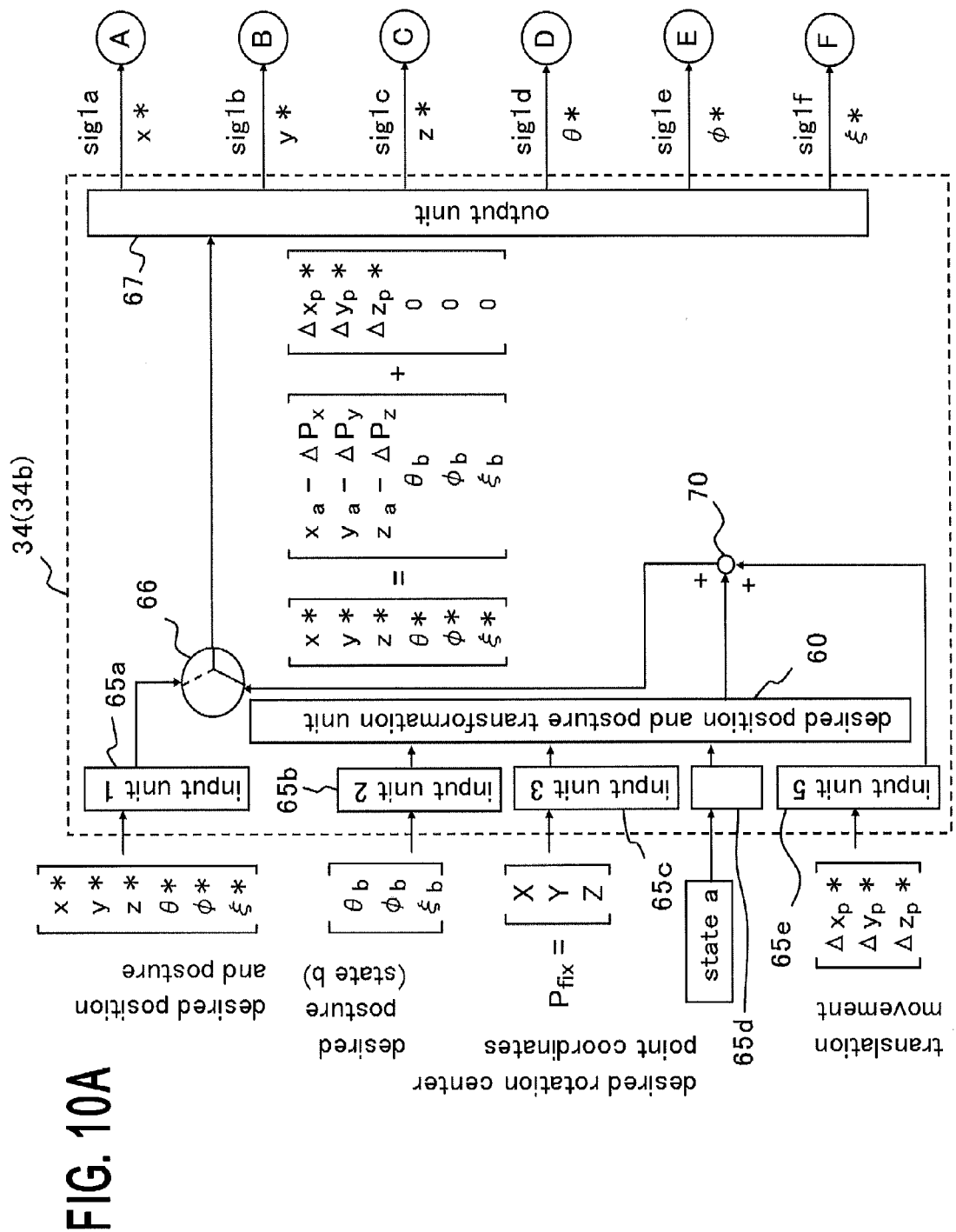
FIG. 10B is a block diagram for explaining the control of the patient platform according to Embodiment 2.
Figure 10B:
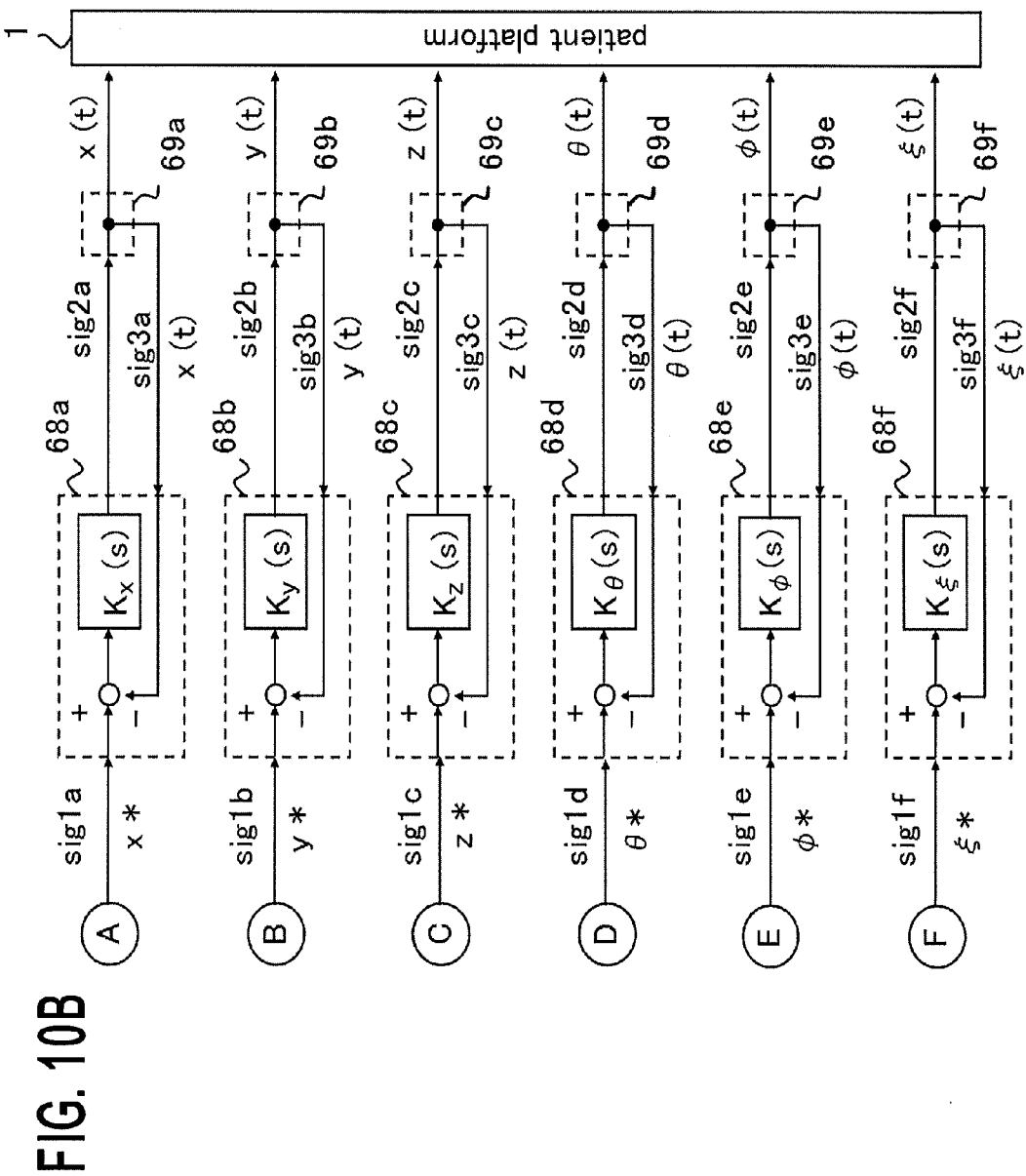

In the case where a positional deviation (coordinate deviation) is caused by an error in the driving device for the patient platform 1, the same flow as that from the step S1 through S8 in FIG. 7 is applied. There will be explained the case where the driving device is controlled by the command signals sig1a through sig1f with which an offset is set. A set of FIG. 10A and FIG. 10B is a block diagram for explaining the control of the patient platform 1 according to Embodiment 2. A set of FIG. 10A and FIG. 10B is different from a set of FIG. 8A and FIG. 8B in Embodiment 1 in that an input unit 65e and a calculation unit 70 are added to the controller 34 (34b), and the desired position and posture $\{x^*, y^*, z^*, \theta^*, \phi^*, \xi^*\}$ is generated by adding $\{\Delta x_p^*, \Delta y_p^*, \Delta z_p^*, 0, 0, 0\}$ to the desired position and posture calculated by the desired position and posture transformation unit 60.

The flow from the step S1 through the step S8 in FIG. 7 is similarly applied; after that, the step S9 is implemented. In the step S9, a translation movement amount $\{\Delta x_p^*, \Delta y_p^*, \Delta z_p^*\}$, which is the difference $P_c(X, Y, Z)$ that is the same as or smaller than the predetermined value and obtained from the coordinates $P_{fix}(X, Y, Z)$ of the desired rotation center point, is added to the desired position and posture $\{x_a-\Delta P_x, y_a-\Delta P_y, z_a-\Delta P_z, \theta_b, \phi_b, \xi_b\}$ calculated in the step S8. The translation movement amount $\{\Delta x_p^*, \Delta y_p^*, \Delta z_p^*\}$ is inputted to the input unit 65e. The calculation unit 70 generates a desired position and posture $\{x^*, y^*, z^*, \theta^*, \phi^*, \xi^*\}$ by adding the translation movement amount $\{\Delta x_p^*, \Delta y_p^*, \Delta z_p^*\}$ to the desired position and posture $\{x_a-\Delta P_x, y_a-\Delta P_y, z_a-\Delta P_z, \theta_b, \phi_b, \xi_b\}$ calculated by the desired position and posture transformation unit 60. Based on the generated desired position and posture $\{x^*, y^*, z^*, \theta^*, \phi^*, \xi^*\}$, the output unit 67 outputs the command signals sig1a through sig1f to driving devices 35 through 40 (refer to FIG. 11) for six axes.

As described above, the compensation amount for the controller of the driving devices 35 through 40 for the patient platform configuration members 3 through 5 becomes $P_{ab}(X, Y, Z) - P_{fix}(X, Y, Z) + P_c(X, Y, Z)$. The controller 34 (34b) generates the rotation drive signal for the rotation unit, based on the desired rotation angle for rotating the patient platform from the state "a", which is the state prior to rotation driving, to the state "b", which is the driving target (desired posture), and generates the translation drive signal for translating the translation unit, by performing compensation of the difference value $(P_{ab}(X, Y, Z) - P_{fix}(X, Y, Z))$ calculated in the step S7 in such a way that the translation movement amount becomes the same as or smaller than the predetermined value.

In some cases, rotating a diseased site on a point that is within a predetermined distance from the desired rotation center point P is eventually equivalent to rotating the diseased site on another rotation center point (an imaginary rotation center point). This will be explained below. It is assumed that the coordinate represented by a one-coordinate system is $q_1$, the coordinates represented by a two-coordinate system is $q_2$, and the translation after $\theta$ rotation is "a" (vector). The one-coordinate system and the two-coordinate system are in the relationship in which, when the one-coordinate system is $\theta$-rotated and then "a"-translated, the one-coordinate system and the two-coordinate system are superimposed on each other; thus, the equation (18) is given.

$$q_1 = R(\theta)q_2 + a \qquad (18)$$

where $R(\theta)$ is a rotation matrix.

When an imaginary rotation center point, which is a fixed point, exists, both a one-coordinate system and a two-coordinate system can be represented with the same coordinates; thus, the coordinates $q_{fix}$ of the fixed point can be obtained as follows. By substituting $q_{fix}$ for $q_1$ and $q_2$ of the equation (18) and rearranging it, the equation (19) is obtained.

$$(I - R(\theta))q_{fix} = a \qquad (19)$$

where I is a unit matrix.

In the case where the inverse matrix $(I-R(\theta))^{-1}$ of $(I-R(\theta))$ exists, the coordinates $q_{fix}$ of the fixed point can be represented as the equation (20).

$$q_{fix} = (I - R(\theta))^{-1} a \qquad (20)$$

For example, in the case where the patient platform is rotated on the Z axis as a center axis and is translated in the Z axis, $(I-R(\theta))^{-1}$ does not exists; therefore, the coordinates $q_{fix}$ of the fixed point cannot be obtained. However, only when rotation and translation are limited on a two-dimensional plane and the rotation angle is not "0", the fixed point exists. In the case where the fixed point exists, the diseased site can be rotated on an imaginary rotation center point.

Based on the desired rotation center point P and the desired rotation angle, the patient platform 1 in Embodiment 2 is driven by combining the rotation drive of the top board 8 and the translation drive performed in such a way that the translation movement amount, of the desired rotation center point P, that is produced by rotation-moving the top board 8 to the desired rotation angle is the same as or smaller than a predetermined value, so that the patient platform 1 can automatically be rotated on a point within a predetermined distance from the desired rotation center point P. As a result, there can efficiently be performed the positioning work for making the position and the posture of a diseased site coincide with those established when a treatment plan is generated.

As is the case with Embodiment 1, regardless of the type of a patient platform such as a bed or a chair, the program, according to Embodiment 2, for implementing the positioning method for the patient platform 1 can be applied even to an already installed patient platform, without hardware modification or additional construction work being carried out. As described above, because of the scalability, the patient platform 1 can readily and automatically be rotated on a point within a predetermined distance from the desired rotation center point P. Therefore, there can readily be performed the positioning work for making the position and the posture of a diseased site coincide with those established when a treatment plan is generated. As a result, the time for preparing treatment can considerably be reduced.

As described above, in the driving type patient platform 1 according to Embodiment 2, there are provided the translation unit 3, 4, and 5 that translate the top board 8 in the X direction, the Y direction, and the Z direction, respectively, in the fixed coordinate system 10 fixed to the installation place; the rotation unit 6, 7, and 8 that rotate the top board 8 in the θ direction around the X axis, the φ direction around the Y axis, and the ξ direction around the Z axis, respectively; and the control device that controls the translation unit 3, 4, and the rotation unit 6, 7, and 8, based on an inputted desired rotation center point P and an inputted desired rotation angle. The control device is provided with the rotation drive signal generation unit that generates the rotation drive signal for moving the top board 8 in a rotating manner from the reference state "a" of the translation unit 3, 4, and 5 and the rotation unit 6, 7, and 8 to a desired rotation angle; and the translation drive signal generation unit that generates the translation drive signal for translating the translation unit 3, 4, and 5 in such a way that the amount of translation movement, of the desired rotation center point P, that is caused by the rotation movement becomes the same as or smaller than a predetermined value. As a result, the patient platform 1 can automatically be rotated on a point within a predetermined distance from the desired rotation center point P, and there can efficiently be performed the positioning work for making the position and the posture of a diseased site coincide with those established when a treatment plan is generated.

Embodiment 3

Embodiment 3 of the present invention is a patient platform provided with a patient platform controller, which is a control device in which the program described in Embodiment 1 is integrated. To date, a patient platform controller has been provided with a suspended patient platform operation terminal, i.e., a so-called pendant-type patient platform operation terminal.

Figure 11:
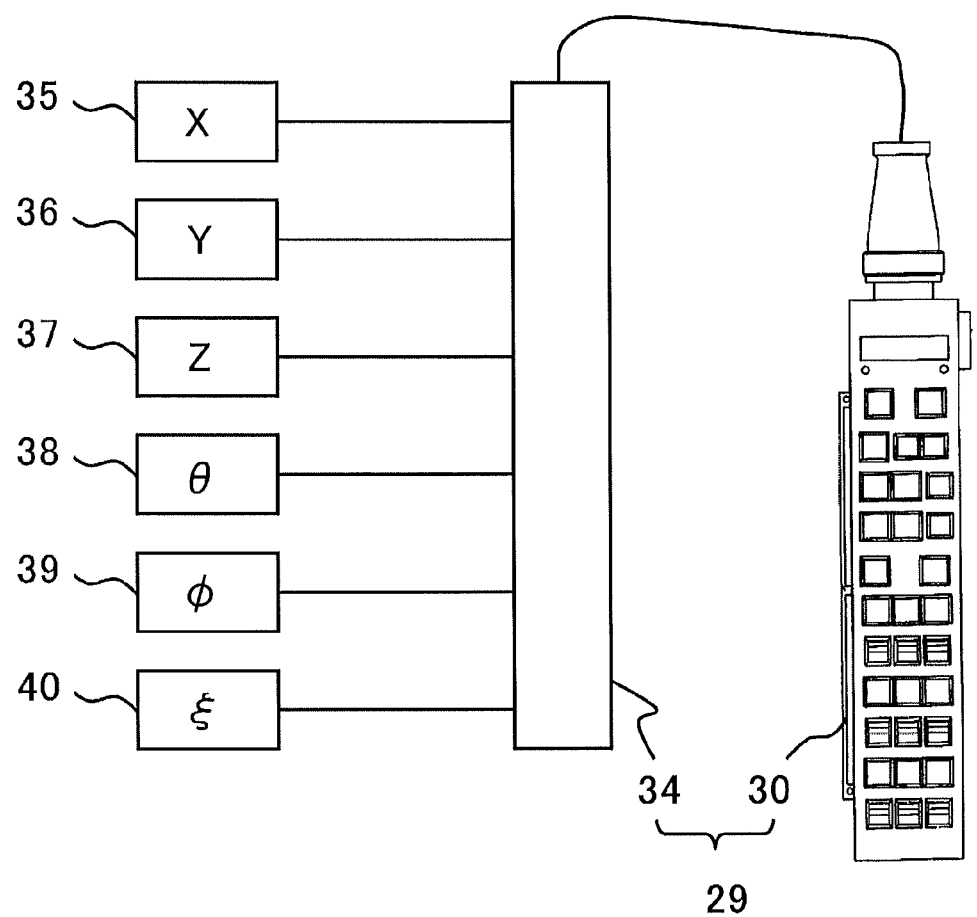
FIG. 11 is a view of a patient platform controller according to Embodiment 3 or 4.
Figure 12A:
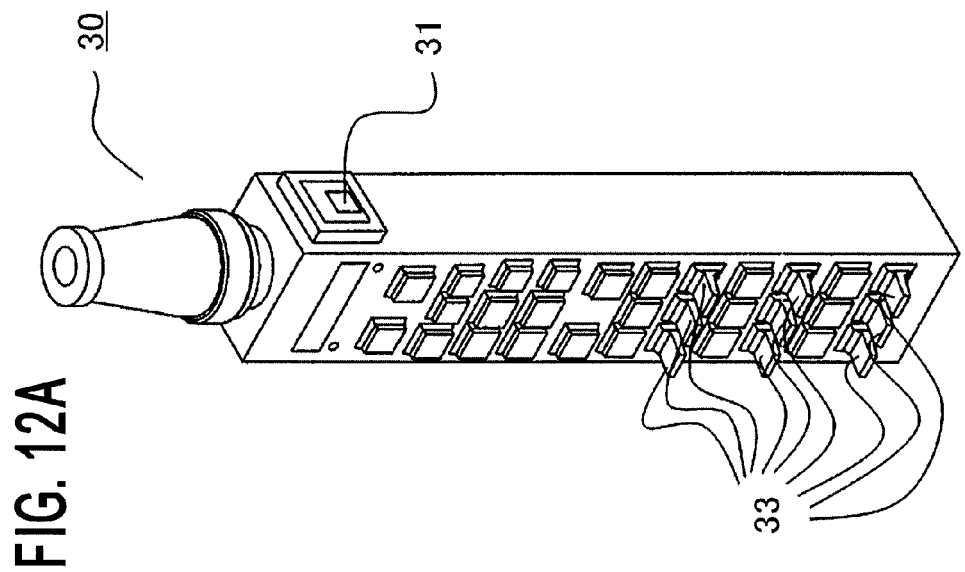
FIG. 12A, FIG. 12B and FIG. 12C are external views of a patient platform operation terminal according to Embodiment 3 or 4.
Figure 12B:
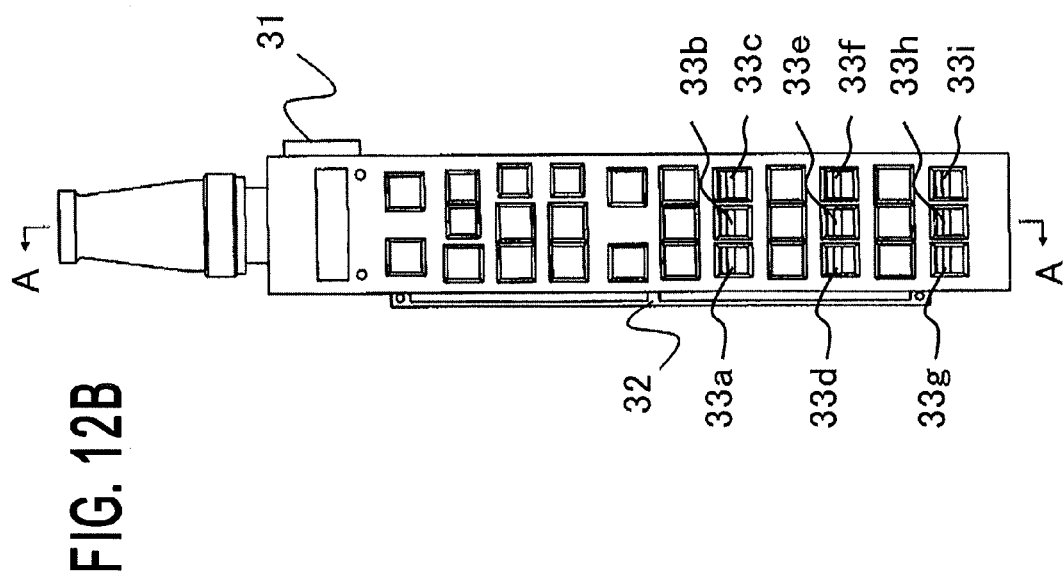
Figure 12C:
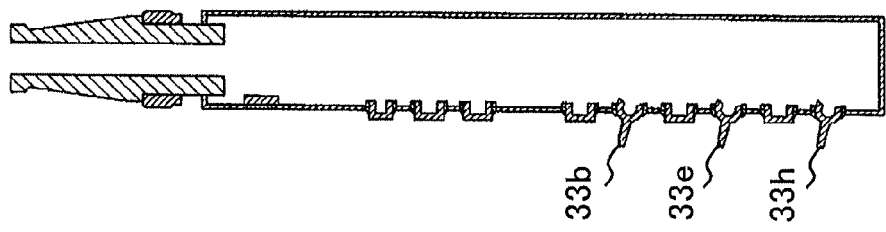

FIG. 11 is a view illustrating a patient platform controller according to Embodiment 3; FIG. 12A, FIG. 12B and FIG. 12C are external views of a pendant-type patient platform operation terminal according to Embodiment 3. FIG. 12A is a bird's eye view; FIG. 12B is an elevation view; FIG. 12C is a cross-sectional view. With reference to FIGS. 11, 12A, 12B and 12C, there will be explained a patient platform controller according to Embodiment 3 of the present invention.

The patient platform controller 29 includes a patient platform operation terminal 30 and a controller 34. Signal information manipulated by means of the patient platform operation terminal 30 is inputted to the controller 34. The program described in Embodiment 1 is integrated in the controller 34. The controller 34 outputs control signals to the driving devices 35 through 40 that drive the patient platform configuration members 3 through 8. The driving device (X translation motor) 35 drives the patient platform configuration member (X-translation member) 3. The driving device (Y translation motor) 36 drives the patient platform configuration member (Y-translation member) 5. The driving device (Z translation motor) 37 drives the patient platform configuration member (Z-translation member) 4. The driving device (yaw rotation motor) 38 drives the patient platform configuration member (yaw rotation member) 6. The driving device (rolling rotation motor) 39 drives the patient platform configuration member (rolling rotation member) 7. The driving device (pitching rotation motor) 40 drives the patient platform configuration member (pitching rotation member) 8.

The patient platform operation terminal 30 is a pendant-type mobile operation terminal for the patient platform 1. The patient platform operation terminal 30 controls the position and the posture of the patient platform 1. An emergency stop button 31 is a stop button utilized in an emergency. By pushing the emergency stop button 31, all the operation of the patient platform 1 can completely be stopped. A hard-wired switch 32 is a circuit-type switch for switching states through physically disconnecting or connecting wiring leads. The patient platform controller 29 is designed in such a way that, because of the hard-wired switch 32, only when an operator grasps the patient platform operation terminal 30, the patient platform 1 can be driven, and when the patient platform operation terminal 30 is released, the operation of the patient platform 1 stops. The lever 33, which is a JOG-drive-mode input device, is a lever switch utilized in the JOG drive mode. The lever 33 is a circuit-type switch for performing switching among three states (stop, movement in a first direction, and movement in a second direction which is a direction opposite to the first direction) through physically disconnecting or connecting wiring leads. By utilizing the levers, manipulation can be performed while the movements of the patient platform and the patient are viewed, without viewing the patient platform operation terminal 30; thus, the operability is enhanced and safe operation can be performed. Reference characters 33a, 33b, and 33c are an X-axis JOG-drive-mode lever, a Y-axis JOG-drive-mode lever, and a Z-axis JOG-drive-mode lever, respectively. Reference characters 33d, 33e, and 33f are a yaw-rotating-axis JOG-drive-mode lever, a rolling-rotation-axis JOG-drive-mode lever, and a pitching-rotation-axis JOG-drive-mode lever, respectively. Reference characters 33g, 33h, and 33i are a new-yaw-rotation JOG-drive-mode lever, a new-rolling-rotation JOG-drive-mode lever, and a new-pitching-rotation JOG-drive-mode lever, respectively. The drive modes will be explained in detail in the next paragraph.

In the patient platform controller 29 according to Embodiment 3 of the present invention, the drive modes are roughly categorized into an automatic drive mode and a JOG drive mode. In the automatic drive mode, a desired state of the patient platform is inputted, as a numerical value, by means of an input device such as a button switch; when the drive start is instructed, the patient platform 1 is driving-controlled so as to be in the desired state. In contrast, in the JOG drive mode, by throwing the JOG-drive-mode lever 33 allocated to each drive axis (driving device), the corresponding axis is driven. For example, when the X-axis JOG-drive-mode lever 33a is tilted upward, the X-translation member 3 is translated in the positive X direction; in contrast, when the X-axis JOG-drive-mode lever 33a is tilted downward, the X-translation member 3 is translated in the negative X direction. The foregoing relationship applies also to the rotation direction. For example, when the yaw-rotation JOG-drive-mode lever 33d is tilted upward, the yaw rotation member 6 is rotated in the positive yaw-rotation direction; in contrast, when the yaw-rotation JOG-drive-mode lever 33d is tilted downward, the yaw rotation member 6 is rotated in the negative yaw-rotation direction. The input signal generated through the JOG-drive-mode lever 33 is inputted to the controller 34; while the lever 33 is connected, the controller 34 outputs a control signal to the driving device of the corresponding axis so that driving is performed at a predetermined constant speed. In this regard, however, when the input through the lever 33 exceeds the driving range of each axis, the controller 34 outputs an upper-limit or a lower-limit control signal. As a result, the length of the connecting time of the lever 33a, 33b, or 33c determines the amount of translation movement; the length of the connecting time of the lever 33d, 33e, or 33f determines the amount of rotation movement.

The patient platform controller 29 according to Embodiment 3 of the present invention has a new automatic drive mode and a new JOG drive mode in addition to the foregoing automatic drive mode and the JOG drive mode. In the new automatic drive mode, when, by use of the program described in Embodiment 1, a desired patient platform posture is inputted as a numerical value by means of an input device such as a button switch and the drive start is instructed, the patient platform 1 is controlled in such a way as to be yaw-rotated, rolling-rotated, and pitching-rotated on the isocenter; as a result, the patient platform 1 is driving-controlled in such a way that the isocenter positions on the top board 8 before and after the drive does not change. In the new JOG drive mode, by use of the program described in Embodiment 1, the JOG-drive-mode lever 33g, 33h, and 33i allocated to the respective rotation drive axis (rotation driving devices) are manipulated. While the lever 33g, 33h, or 33i is tilted, the corresponding portion of the patient platform 1 is rotated on the corresponding axis at a predetermined constant angular velocity. In other words, by throwing the lever 33g, 33h, or 33i, the patient platform 1 is driving-controlled in the corresponding rotation direction, as if a focused point (e.g., isocenter) is a rotation center point. As a result, the patient platform 1 is driving-controlled in such a way that the position of the focused point (e.g., isocenter) on the top board 8, i.e., the desired point 22 is always fixed.

Regardless of the type of a patient platform such as a bed or a chair, the patient platform controller 29 according to Embodiment 3 of the present invention can be applied even to an already installed patient platform, without hardware modification or additional construction work being carried out. As described above, because of the scalability, a diseased site can be rotated on a desired point P in a simply and high-operability manner. Moreover, utilizing an isocenter as the desired center point P of the rotation control, the posture of the patient platform 1 can be JOG-driven while always keeping the isocenter on the top board 8; therefore, there can readily be performed the positioning work for making the position and the posture of a diseased site coincide with those established when a treatment plan is generated. As a result, the time for preparing treatment can considerably be reduced.

The patient platform 1 provided with the patient platform controller 29 according to Embodiment 3 implements a positioning method in which rotation drive and translation drive are combined; therefore, a diseased site can be rotated on a desired point P in a high-operability manner. Moreover, utilizing an isocenter as the desired center point P of the rotation control, the posture of the patient platform 1 can be automatically driven or JOG-driven while always keeping the isocenter on the top board 8; therefore, there can readily be performed the positioning work for making the position and the posture of a diseased site coincide with those established when a treatment plan is generated. As a result, the time for preparing treatment can considerably be reduced.

The desired center point P for the rotation control may be determined by a program; however, the desired center point P may be changed by manipulating a button through the patient platform operation terminal 30. For example, as the desired center point P for the rotation control, in addition to the isocenter, positional information such as the landmark for each patient is registered as a parameter in the program; the positional information items are selectively utilized.

In addition, there has been explained an example where the program described in Embodiment 1 is integrated in the controller 34; however, the controller 34 may be incorporated in the patient platform operation terminal 30.

Embodiment 4

Embodiment 4 of the present invention is a patient platform provided with a patient platform controller, which is a control device in which the program described in Embodiment 2 is integrated. A patient platform controller according to Embodiment 4 is similar to the patient platform controller (FIGS. 11, 12A, 12B and 12C) according to Embodiment 3. The new automatic drive mode and the new JOG drive mode will be explained.

In the new automatic drive mode, when, by use of the program described in Embodiment 2, a desired patient platform posture is inputted as a numerical value by means of an input device such as a button switch and the drive start is instructed, the patient platform 1 is controlled in such a way as to be yaw-rotated, rolling-rotated, and pitching-rotated on the desired rotation center point P; as a result, the patient platform 1 is driving-controlled in such a way that the patient platform 1 is rotated on a point within a predetermined distance from the desired center point P. In the new JOG drive mode, by use of the program described in Embodiment 2, the JOG-drive-mode lever 33g, 33h, and 33i allocated to the respective rotation drive axis (rotation driving devices) are manipulated. By throwing the lever 33g, 33h, or 33i, the patient platform 1 is driving-controlled in such a way that the posture of the diseased site is rotated in the corresponding rotation direction, and the position of the diseased site is within a predetermined distance from the desired rotation center point P. Normally, the distance of a positional deviation (coordinate deviation) caused by an error in the driving device for the patient platform 1 is short; thus, even in the case where a positional deviation (coordinate deviation) caused by an error in the driving device for the patient platform 1 occurs, there exists no obstacle to the positioning work in the JOG drive mode.

As is the case with Embodiment 3, regardless of the type of a patient platform such as a bed or a chair, the patient platform controller 29 according to Embodiment 4 of the present invention can be applied even to an already installed patient platform, without hardware modification or additional construction work being carried out. As described above, because of the scalability, the patient platform 1 can readily and automatically be rotated on a point within a predetermined distance from the desired rotation center point P. Therefore, there can readily be performed the positioning work for making the position and the posture of a diseased site coincide with those established when a treatment plan is generated. As a result, the time for preparing treatment can considerably be reduced.

As is the case with Embodiment 3, the patient platform 1 provided with the patient platform controller 29 according to Embodiment 4 implements a positioning method in which rotation drive and translation drive are combined; therefore, the posture of the diseased site can be rotated with high operability, and the position of the diseased site can be controlled so as to be within a predetermined distance from the desired rotation center point P. Because the posture of the patient platform 1 can be automatically driven or JOG-driven, there can readily be performed the positioning work for making the position and the posture of a diseased site coincide with those established when a treatment plan is generated. As a result, the time for preparing treatment can considerably be reduced.

In the case where the driving device is controlled through automatic drive by use of a control signal in which an offset is set, by making it possible to change the offset by button manipulation through the patient platform operation terminal 30, for example, in the case where a diseased site appears at the bottom of the captured image of the X-ray image-capturing device, there can be performed with high operability the operation in which, by rotating the posture of the diseased site on the desired rotation center point P, the whole diseased site can be moved to the center of the captured image. In such a way as described above, it is made possible to move the diseased site to a desired position in a shorter time than that in the case where the diseased site is moved to the center of the captured image and then is rotated on the desired rotation center point P.

As is the case with Embodiment 3, the desired point P for rotation control may preliminarily be determined in the program; however, the desired point P may be changed by button manipulation through the patient platform operation terminal 30. The controller 34 may be incorporated in the patient platform operation terminal 30.

Embodiment 5

In Embodiments 1 through 4, it has been described how the rotation drive signal and the translation drive signal for the driving type patient platform 1, i.e., the command values of the command signals sig1*a* through sig1*f* for the driving type patient platform 1 should be generated in order to realize the rotation on the desired rotation center point P. In Embodiments 1 through 4, the rotation drive signal and the translation drive signal generated by the controller 34 are utilized as a feed-forward control signal. In Embodiment 5, a completely different approach will be taken.

Figure 13B:
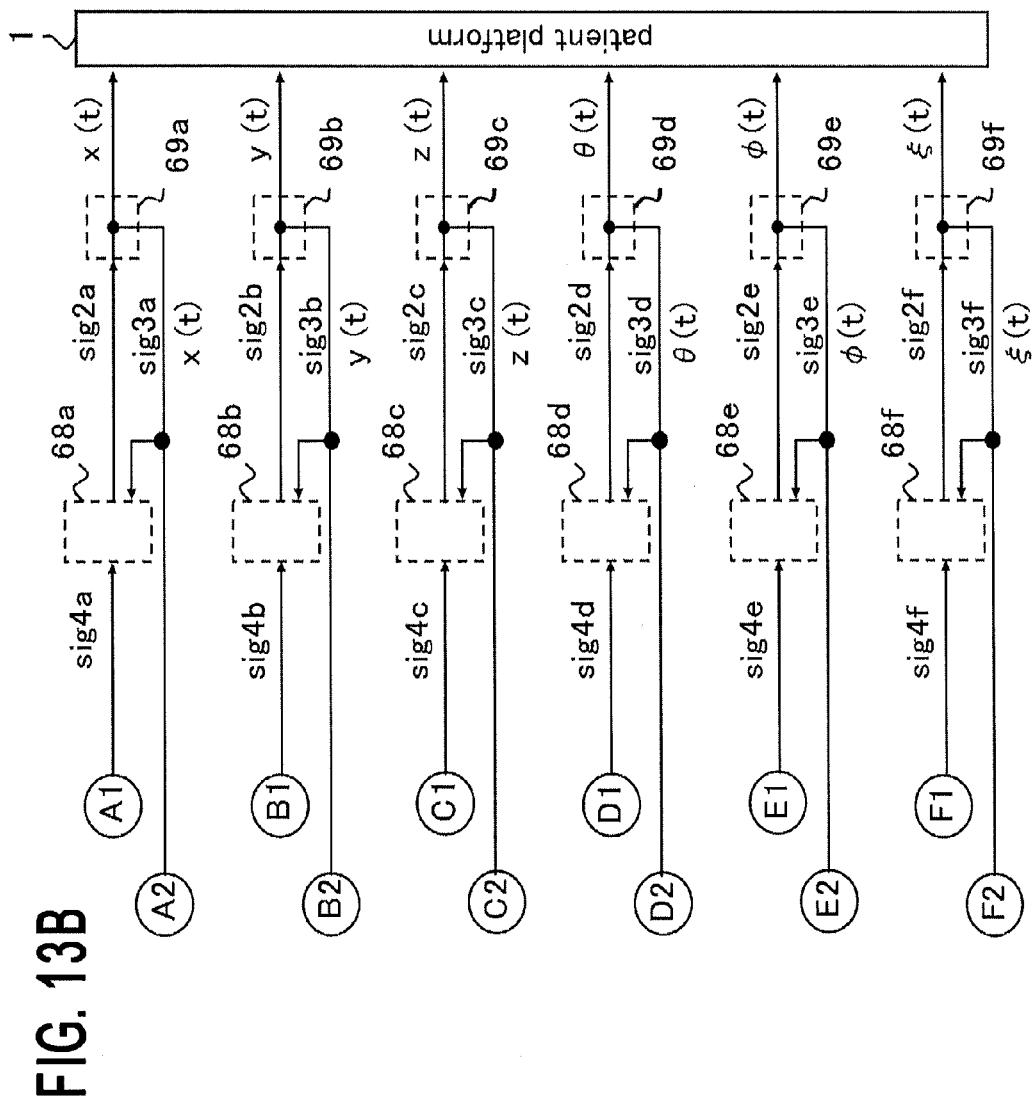
FIG. 13B is a block diagram for explaining the control of a patient platform according to Embodiment 5.

In Embodiment 5, by implementing feedback control, the foregoing problems are solved. The method will be specifically described with reference to FIGS. 13A and 13B. A set of FIG. 13A and FIG. 13B is a block diagram for explaining the control of the patient platform 1 according to Embodiment 5. A set of FIG. 13A and FIG. 13B is different from a set of FIG. 8A and FIG. 8B in Embodiment 1 in that an adjusting unit 73 (73*a*) is added to the controller 34 (34*c*) and the driving devices 35 through 40 are controlled by difference command signals sig4*a* through sig4*f* outputted from the adjusting unit 73 (73*a*). As described above, in general, a detection signal from an encoder or the like is fed back to a motor driver, and the driver controls a motor. In Embodiment 5 of the present invention, a detection signal from an encoder or the like is inputted to the controller 34 (34*c*), and the controller 34 (34*c*) controls a motor.

The adjusting unit 73 (73*a*) of the controller 34 (34*c*) compares the present state $\{x(t)$ through $\xi(t)\}$ (position posture) of the patient platform 1 with the desired position and posture $\{x^*, y^*, z^*, \theta^*, \phi^*, \xi\}$ so that the command values of the difference command signals sig4*a* through sig4*f* such as the torque command and the like are generated in according to the difference. As a result, an effect the same as that demonstrated in each of Embodiments 1 through 4 can be obtained.

The adjusting unit 73 (73*a*) is provided with respective feedback systems having transfer functions 74*a* through 74*f* corresponding to the driving devices (motors) 35 through 40. Signals for realizing the desired position and posture $\{x^*, y^*, z^*, \theta^*, \phi^*, \xi^*\}$ and the detection signals sig3*a* through sig3*f* obtained by detecting the present state $\{x(t)$ through $\xi(t)\}$ of the patient platform 1 are inputted to the respective feedback systems. In this situation, in FIGS. 13A and 13B, the reference characters added to FIGS. 8A and 8B are as follows. The transfer function 74*a* and the difference command signal sig4*a* are related to the driving device (X translation motor) 35. The transfer function 74*b* and the difference command signal sig4*b* are related to the driving device (Y translation motor) 36. The transfer function 74*c* and the difference command signal sig4*c* are related to the driving device (Z translation motor) 37. The transfer function 74*d* and the difference command signal sig4*d* are related to the driving device (yaw rotation motor) 38. The transfer function 74*e* and the difference command signal sig4*e* are related to the driving device (rolling rotation motor) 39. The transfer function 74*f* and the difference command signal sig4*f* are related to the driving device (pitching rotation motor) 40.

Figure 14B:
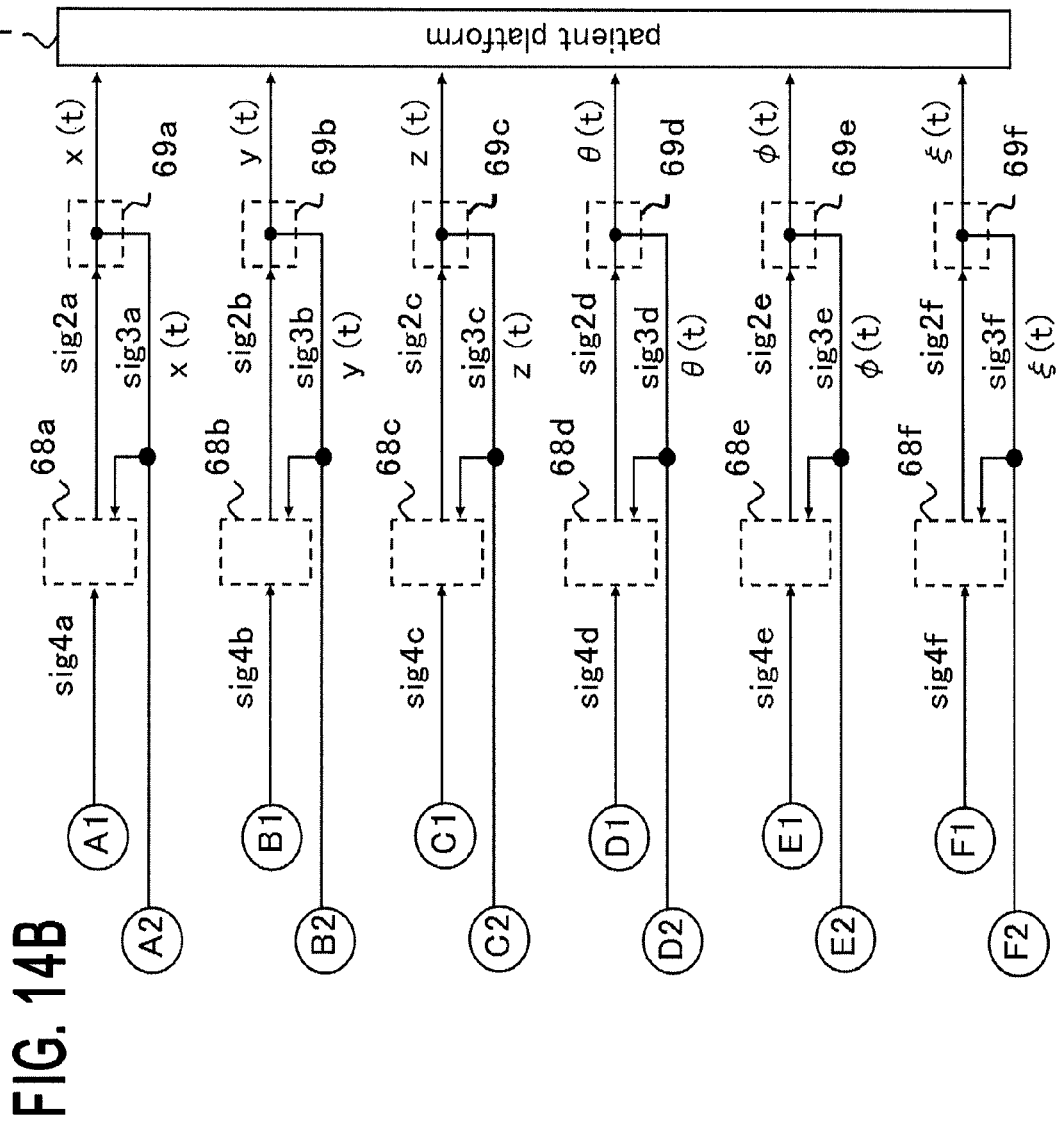
FIG. 14B is another block diagram for explaining the control of the patient platform according to Embodiment 5.

It is conceivable that, in the controller 34, a dead band is set in a unit where the command value of the torque command or the like is generated. A set of FIG. 14A and FIG. 14B is another block diagram for explaining the control of the patient platform 1 according to Embodiment 5. A set of FIG. 14A and FIG. 14B is different from a set of FIG. 13A and FIG. 13B in that the transfer functions in the adjusting unit 73 (73*b*) of the controller 34 (34*d*) are transfer functions 75*a* through 75*f* in which dead bands are set. The P-control where a dead band is set is expressed by the following equation. The equation (21) represents the characteristics of the transfer function 75*a*, and it represents an example where a dead band is provided in the P-control of the driving device (X translation motor) 35.

$$K_x(s) = \begin{cases} K_P & \text{if } |x(t) - x^*| > \varepsilon \\ 0 & \text{if } |x(t) - x^*| \le \varepsilon \end{cases} \quad (21)$$

where $K_p$ is a gain, and $\varepsilon$ is a parameter for determining the largeness of the dead band. By providing a dead band, chattering of a motor can be prevented.

In each of the driving devices 36 through 40 other than the driving device (X translation motor) 35, a dead band is provided in the P-control in the same manner as represented by the equation (21). As the equation representing the characteristics of the transfer function 75*b* that corresponds to the driving device (Y translation motor) 36, the equation obtained by replacing "x" in the equation (21) by "y" may be utilized. As the equation representing the characteristics of the transfer function 75*c* that corresponds to the driving device (Z translation motor) 37, the equation obtained by replacing "x" in the equation (21) by "z" may be utilized. As the equation representing the characteristics of the transfer function 75d that corresponds to the driving device (yaw rotation motor) 38, the equation obtained by replacing "x" in the equation (21) by may be utilized. As the equation representing the characteristics of the transfer function 75e that corresponds to the driving device (rolling rotation motor) 39, the equation obtained by replacing "x" in the equation (21) by "φ" may be utilized. As the equation representing the characteristics of the transfer function 75f that corresponds to the driving device (pitching rotation motor) 40, the equation obtained by replacing "x" in the equation (21) by "ξ" may be utilized.

The explanation for Embodiment 5 has been performed with reference to a set of FIG. 13A and FIG. 13B or a set of FIG. 14A and FIG. 14B, which is a modification of a set of FIG. 8A and FIG. 8B in Embodiment 1; this explanation can be applied to a modification of a set of FIG. 10A and FIG. 10B in Embodiment 2. There is utilized a controller obtained by replacing the control of the patient platform 1 from the output unit 67 in FIGS. 10A and 10B by the control of the patient platform 1 from the output unit 67 in a set of FIG. 13A and FIG. 13B or a set of FIG. 14A and FIG. 14B. As a result, an effect the same as that demonstrated in each of Embodiments 2 and 4 can be obtained.

Because of the foregoing configuration by the patient platform 1 according to Embodiment 5, the program for implementing the positioning method for the patient platform 1, and the patient platform controller 29, the driving type patient platform 1 can automatically be rotated on a point that is within a predetermined distance from the desired rotation center point P; there can efficiently be performed the positioning work for making the position and the posture of a diseased site coincide with those established when a treatment plan is generated.

Embodiment 6

In Embodiment 6, there will be described a more irregular method than in Embodiment 5. In Embodiment 6, the posture and the position of the patient platform 1 are separately controlled. The target posture of the patient platform 1 is given explicitly. Accordingly, as is the case with a conventional technology, the posture of the patient platform 1 may independently be controlled. What matters is how to control the position of the patient platform. The method will be described below.

The controller 34 comprehends the present actual state $\{x(t), y(t), z(t), \theta(t), \phi(t), \xi(t)\}$ of the patient platform, based on the detection signals sig3a through sig3f from encoders or the like. In this situation, the controller 34 has the coordinate transformation unit C2 (the second coordinate transformation unit), represented by the equation (13), for performing transformation of the coordinate system from "the coordinate system $o_{obj}$ fixed to the top board" (moving coordinate system) into "the coordinate system $O_{fix}$ fixed to the treatment room" (fixed coordinate system); therefore, it can always be calculated where a certain position on the top board is situated in the treatment room.

The method of inputting the desired rotation center point is completely the same as the method in each of Embodiments 1 through 5. The coordinates $p_a$ in a moving coordinate system and the coordinates $P_{fix}$ in a fixed coordinate system of the desired rotation center point at a time before driving (in the state "a") are inputted to the controller 34. In the state "b", instead of inputting the target posture of the patient platform, the present state is inputted.

Based on the present state $\{x(t), y(t), z(t), \theta(t), \phi(t), \xi(t)\}$ of the patient platform and the coordinates $p_a$ of the desired rotation center point in the moving coordinate system at a time of the initial state (state "a"), the controller 34 calculates the position coordinates $P_{ab}$ of the desired rotation center point in the fixed coordinate system at the present time (state "b"). Furthermore, the controller 34 calculates the difference between the position coordinates of the desired rotation center point in the fixed coordinate system at the present time (state "b") and the coordinates $P_{fix}$ in the fixed coordinate system at the initial state (in the state "a"), and compensates the translation drive signal for the patient platform in such a way that the absolute value of the difference becomes the sane as or smaller than a predetermined value.

Because of the foregoing configuration by the patient platform 1 according to Embodiment 6, the program for implementing the positioning method for the patient platform 1, and the patient platform controller 29, the driving type patient platform 1 can automatically be rotated on a point that is within a predetermined distance from the desired rotation center point P; therefore, there can efficiently be performed the positioning work for making the position and the posture of a diseased site coincide with those established when a treatment plan is generated.

Embodiment 7

Figure 15:
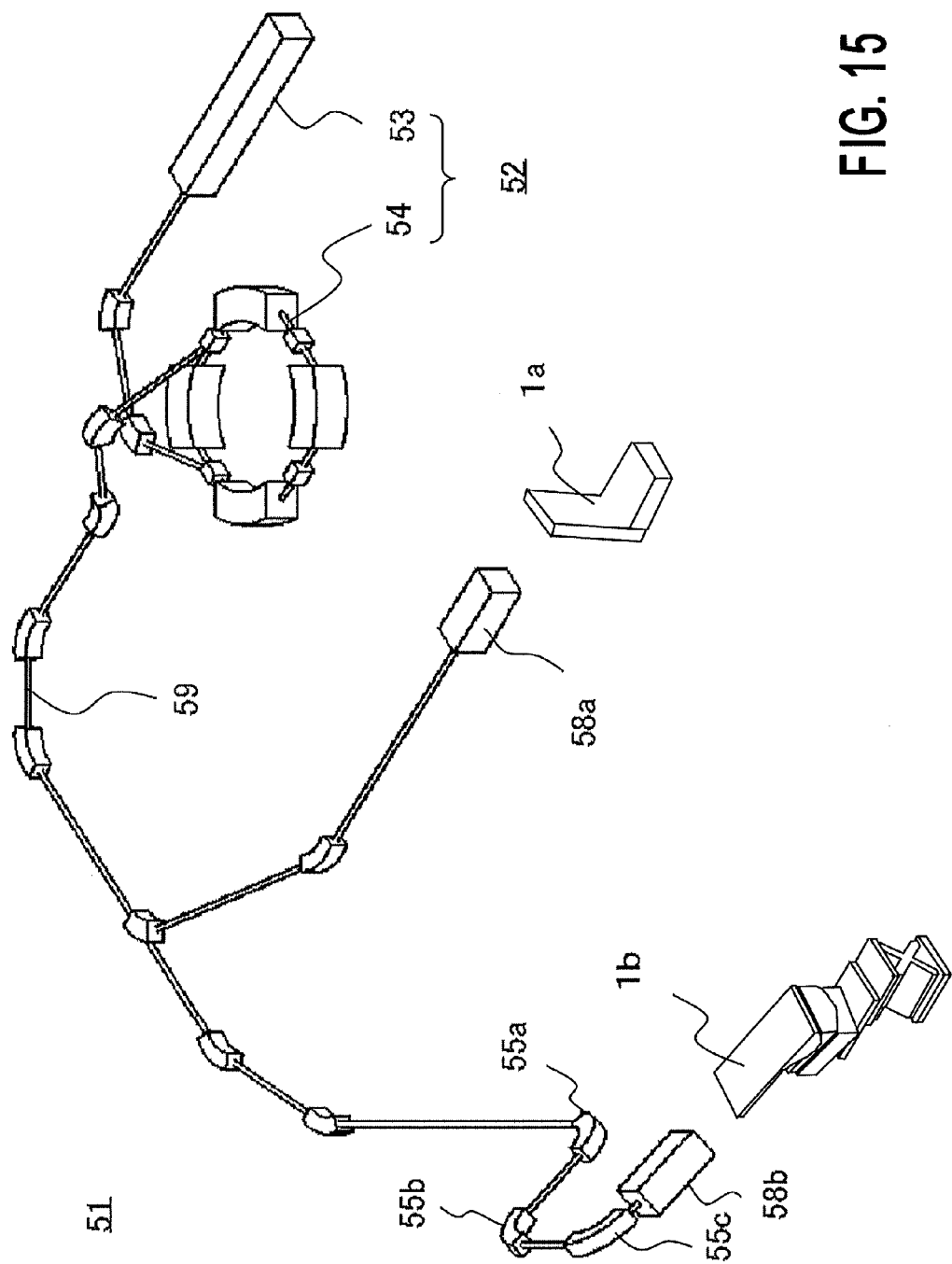
FIG. 15 is a configuration diagram illustrating a particle beam therapy system according to Embodiment 7.

Embodiment 7 of the present invention is a particle beam therapy system provided with the patient platform 1 described in each of Embodiments 1 through 6. FIG. 15 is a schematic configuration diagram illustrating a particle beam therapy system according to Embodiment 7 of the present invention. A particle beam therapy system 51 includes an ion beam generation apparatus 52, an ion beam transport system 59, particle beam irradiation apparatuses 58a and 58b, and patient platforms 1a and 1b on which a patient is placed and fixed. The ion beam generation apparatus 52 includes an ion source (unillustrated), a prestage accelerator 53, and a synchrotron 54. The particle beam irradiation apparatus 58b is provided in a rotating gantry (unillustrated). The particle beam irradiation apparatus 58a is provided in a treatment room where no rotating gantry is installed. The function of the ion beam transport system 59 is to achieve communication between the synchrotron 54 and the particle beam irradiation apparatuses 58a and 58b. A portion of the ion beam transport system 59 is provided in the rotating gantry (unillustrated), and in that portion, there are included a plurality of deflection electromagnets 55a, 55b, and 55c.

A charged particle beam, which is a particle beam such as a proton beam generated in ion source, is accelerated by the prestage accelerator 53 and enters the synchrotron 54. The particle beam is accelerated to have predetermined energy. The charged particle beam launched from the synchrotron 54 is transported to the particle beam irradiation apparatuses 58a and 58b by way of the ion beam transport system 59. The particle beam irradiation apparatuses 58a and 58b each irradiate the charged particle beam onto the irradiation subject (unillustrated) of a patient placed on the patient platform 1a or 1b. In FIG. 15, the patient platform 1a is a chair type, and the patient platform 1b is a bed type.

The particle beam therapy system 51 according to Embodiment 7 is provided with the patient platform 1 for which there is implemented a positioning method in which rotation drive and translation drive are combined; therefore, there can efficiently be performed the positioning work for making the position and the posture of a diseased site coincide with those established when a treatment plan is generated. As a result, the time for preparing treatment can considerably be reduced. Moreover, the throughput of the particle beam therapy system can be improved.

The driving type patient platform, the control device for the driving type patient platform, and the control program for the driving type patient platform described in each of Embodiments 1 through 6 can be applied not only to a particle beam therapy system but also to a radiation therapy system that irradiates an X-ray or the like.

Various modifications and alterations of this invention will be apparent to those skilled in the art without departing from the scope and spirit of this invention, and it should be understood that this is not limited to the illustrative embodiments set forth herein.

What is claimed is:

1. A driving type patient platform having a top board on which an irradiation subject is fixed when a radiation is irradiated onto the irradiation subject, the driving type patient platform comprising:
 a translation unit that translates the top board in the X direction, the Y direction, and the Z direction, respectively, in a fixed coordinate system fixed to an installation place where the driving type patient platform is installed;
 a rotation unit that rotates the top board in the θ direction around the X axis, the φ direction around the Y axis, and the ξ direction around the Z axis, respectively; and
 a control device that controls the translation unit and the rotation unit, based on an inputted desired rotation center point and an inputted desired rotation angle,
 wherein the control device is provided with a rotation drive signal generation unit that generates a rotation drive signal for performing rotation movement of the top board from the reference position states of the translation unit and the rotation unit to the desired rotation angle; and a translation drive signal generation unit that generates a translation drive signal for translating the translation unit, concurrently with performing the rotation movement, in such a way that the amount of translation movement of the desired rotation center point, that is caused by the rotation movement is maintained within a predetermined value.

2. The driving type patient platform according to claim 1, wherein the translation drive signal generation unit generates a translation drive signal for translating the translation unit in such a way that the amount of translation movement of the desired rotation center point, that is caused by the rotation movement is compensated.

3. The driving type patient platform according to claim 2, wherein the translation drive signal generation unit is provided with a unit that generates the coordinates ($p_a$) to be obtained by coordinate-transforming the coordinates ($P_{fix}$) of the desired rotation center point in the fixed coordinate system in the reference position states into the moving coordinate system fixed to the top board; a unit for transforming the coordinate ($p_a$) into coordinate ($P_{ab}$), where coordinate ($P_{ab}$) is the coordinate of the point ($p_a$) assumed to have rotation-moved to the desired rotation angle along with the top board, expressed in the fixed coordinate system; and a unit that generates a translation drive signal for compensating the moving amount of the translation unit in the respective directions, based on the difference between the coordinates ($P_{fix}$) and the coordinates ($P_{ab}$).

4. The driving type patient platform according to claim 1, wherein the control device comprises a patient platform operation terminal for inputting, as a numerical value, the desired rotation angle for the irradiation subject.

5. The driving type patient platform according to claim 1, wherein the control device comprises a patient platform operation terminal; and the patient platform operation terminal comprises inputting devices each corresponding to the rotation axis of the rotation unit, wherein the translation unit and the rotation unit are driven when the corresponding inputting device is being connected.

6. A driving type patient platform control program for generating, by means of a computer, a control signal for driving a driving type patient platform having a top board on which an irradiation subject is fixed when a radiation is irradiated onto the irradiation subject,
 wherein the driving type patient platform has a translation unit that translates the top board in the X direction, the Y direction, and the Z direction, respectively, in a fixed coordinate system fixed to an installation place where the driving type patient platform is installed; and a rotation unit that rotates the top board in the θ direction around the X axis, the φ direction around the Y axis, and the ξ direction around the Z axis, respectively, and
 wherein the driving type patient platform control program functions as a rotation drive signal generation unit that outputs to the rotation unit a rotation drive signal for performing rotation movement of the top board from the reference position states of the translation unit and the rotation unit to the desired rotation angle, based on an inputted desired rotation center point and an inputted desired rotation angle, and as a translation drive signal generation unit that outputs to the translation unit a translation drive signal for translating the translation unit, concurrently with performing the rotation movement, in such a way that the amount of translation movement, of the desired rotation center point, that is caused by the rotation movement is maintained within a predetermined value.

7. The driving type patient platform control program according to claim 6, wherein the translation drive signal generation unit outputs to the translation unit a translation drive signal for translating the translation unit in such a way that the amount of translation movement of the desired rotation center point, that is caused by the rotation movement is compensated.

8. The driving type patient platform control program according to claim 7, wherein the translation drive signal generation unit implements a step of generating the coordinates ($p_a$) to be obtained by coordinate-transforming the coordinates ($P_{fix}$) of the desired rotation center point in the fixed coordinate system in the reference position states into the moving coordinate system fixed to the top board; a step of transforming the coordinate ($p_a$) into coordinate ($P_{ab}$), where coordinate ($P_{ab}$) is the coordinate of the point ($p_a$) assumed to have rotation-moved to the desired rotation angle along with the top board, expressed in the fixed coordinate system; and a step of generating a translation drive signal for compensating the moving amounts of the translation unit in the respective directions, based on the difference between the coordinates ($P_{fix}$) and the coordinates ($P_{ab}$).

9. A driving type patient platform control device programmed with the driving type patient platform control program according to claim 6, wherein the driving type platform control device comprises a patient platform operation terminal for inputting, as a numerical value, the desired rotation angle for the irradiation subject.

10. A driving type patient platform control device including the driving type patient platform control program according to claim 6, wherein the driving type patient platform control device comprises inputting devices each corresponding to the rotation axis of the rotation unit, wherein the translation unit and the rotation unit are driven when the corresponding inputting device is being connected.

11. A particle beam therapy system comprising:
an ion beam generation apparatus that generates a charged particle beam and accelerates the charged particle beam by means of an accelerator until the charged particle beam acquires a predetermined energy;
an ion beam transport system that transports the charged particle beam accelerated by the ion beam generation apparatus;
a particle beam irradiation apparatus that irradiates the charged particle beam transported by the ion beam transport system onto an irradiation subject; and
a driving type patient platform having a top board on which the irradiation subject is fixed,
wherein the driving type patient platform is the driving type patient platform according to claim 1.

12. The driving type patient platform according to claim 2, wherein the control device comprises a patient platform operation terminal for inputting, as a numerical value, the desired rotation angle for the irradiation subject.

13. The driving type patient platform according to claim 2, wherein the control device comprises a patient platform operation terminal; and the patient platform operation terminal comprises inputting devices each corresponding to the rotation axis of the rotation unit, wherein the translation unit and the rotation unit are driven when the corresponding inputting device is being connected.

14. The driving type patient platform according to claim 3, wherein the control device comprises a patient platform operation terminal; and the patient platform operation terminal comprises inputting devices each corresponding to the rotation axis of the rotation unit, wherein the translation unit and the rotation unit are driven when the corresponding inputting device is being connected.

15. A driving type patient platform control device including the driving type patient platform control program according to claim 7, wherein the driving type patient platform control device comprises inputting devices each corresponding to the rotation axis of the rotation unit, wherein the translation unit and the rotation unit are driven when the corresponding inputting device is being connected.

16. A driving type patient platform control device including the driving type patient platform control program according to claim 8, wherein the driving type patient platform control device comprises inputting devices each corresponding to the rotation axis of the rotation unit, wherein the translation unit and the rotation unit are driven when the corresponding inputting device is being connected.

* * * * *